US007078499B2

(12) United States Patent
Odedra et al.

(10) Patent No.: US 7,078,499 B2
(45) Date of Patent: Jul. 18, 2006

(54) NUCLEOTIDE ANALOGUES COMPRISING A REPORTER MOIETY AND A POLYMERASE ENZYME BLOCKING MOIETY

(75) Inventors: Raj Odedra, Amersham (GB); Adrian Simmonds, Amersham (GB); Lee Pickering, Amersham (GB)

(73) Assignee: GE Healthcare UK Limited, Amersham (GB)

( * ) Notice: Subject to any disclaimer, the term of this patent is extended or adjusted under 35 U.S.C. 154(b) by 86 days.

(21) Appl. No.: 10/276,759

(22) PCT Filed: May 31, 2001

(86) PCT No.: PCT/GB01/02402

§ 371 (c)(1),
(2), (4) Date: Mar. 24, 2003

(87) PCT Pub. No.: WO01/92284

PCT Pub. Date: Dec. 6, 2001

(65) Prior Publication Data

US 2003/0194722 A1    Oct. 16, 2003

(30) Foreign Application Priority Data

Jun. 1, 2000   (GB) .................................. 0013276.1

(51) Int. Cl.
*C12Q 1/68* (2006.01)
*C07H 21/04* (2006.01)
*C07H 19/04* (2006.01)

(52) U.S. Cl. ............... 536/22.1; 536/25.32; 536/25.31; 536/26.6; 536/28.6; 536/28.4; 536/27.22; 536/124; 544/277; 514/45; 435/6; 435/7.92; 435/7.94

(58) Field of Classification Search ............... 536/22.1, 536/25.32, 25.31, 26.6, 27.6, 28.4, 27.22, 536/124; 544/277; 514/45; 435/6, 7.92, 435/7.94
See application file for complete search history.

(56) References Cited

U.S. PATENT DOCUMENTS 5,268,486 A    12/1993  Waggoner et al.
5,681,940 A    10/1997  Wang et al.
6,147,205 A *  11/2000  McGall et al. ........... 536/25.31

OTHER PUBLICATIONS

Confalone,"The use of heterocyclic chemistry in the synthesis of natural and unnatural products." J. Heterocyclic Chem. vol. 27 pp. 31-46, 1990.*
Prober, J. M., et al. "A System for Rapid DNA Sequencing with Fluorescent chain-Terminating Dideoxynucleotides" Science, American Association for the Advancement of Science, US vol. 238, No. 4825, Oct. 16, 1987, pp. 336-341.

(Continued)

*Primary Examiner*—Shaojia Anna Jiang
*Assistant Examiner*—Devesh Khare
(74) *Attorney, Agent, or Firm*—Yonggang Ji

(57) ABSTRACT

Nucleotides comprising a reporter moiety and a polymerase enzyme blocking moiety in which the reporter moiety does not also act as a polymerase enzyme blocking moiety are described. Also described are compounds of Formula (I): wherein W is a phosphate group, B is a base, Y is a linker comprising an enzyme-cleavable group, $R^2$ is a reporter moiety, $R^3$ is selected from H or OH, Z and Z' are selected from H, OH, or a group $X—R^1$, wherein X is a linker comprising an enzyme-cleavable group and $R^1$ is a polymerase enzyme blocking group, provided that at least one of Z and Z' is $X—R^1$.

15 Claims, 11 Drawing Sheets

OTHER PUBLICATIONS

Confalone, P. N. "The Use of heterocyclic chemistry in the synthesis of natural and unnatural products" Journal of Heterocyclic Chemistry, Heterocorporation, Provo, US vol. 27, 1990, pp. 31-46.

Casalnuovo, A. L., et al. "Palladium-Catalyzed Alkylations in Aqueous Media" Journal of the American Chemical Society, American Chemical Society, Washington, DC, US vol. 112, No. 11, May 23, 1990, pp. 4324-4330.

Sauer, M., et al. "Detection and Identification of Single Dye Labeled Mononucleotide Molecules Released from an Optical Fiber in a Microcapillary: Firststeps Towards a New Single Molecule DNA Sequencing Technique" Physical Chemistry Chemical Physics, Royal Society of Chemistry, Cambridge, GB vol. 1, No. 10, May 15, 1999, pp. 2471-2477.

* cited by examiner

NUCLEOTIDE ANALOGUES COMPRISING A REPORTER MOIETY AND A POLYMERASE ENZYME BLOCKING MOIETY

FIELD OF THE INVENTION

The present invention relates to nucleoside and nucleotide analogues. In particular, the invention relates to nucleotide analogues having enzyme-cleavable blocking and reporter groups positioned on separate parts of the nucleotide.

BACKGROUND OF THE INVENTION

Recent improvements in DNA sequencing techniques have sought to meet the increasing demands of large scale sequencing. Increasingly, methods in which the template nucleic acid molecules are attached to a solid surface are being developed (see, for example, U.S. Pat. No. 5,302,509 and U.S. Pat. No. 5,547,839). Such methods dispense with the need for an electrophoretic separation step and, with he use of optical detection technologies (see, for example, Nie et al. Annu. Rev. Biophys. Biomol. Struct. 1997, 26: 567–96), aim to allow sequencing information at the level of a single molecule to be obtained. This has the further potential for multiple samples to be analysed simultaneously.

One example of such methods is Base Addition Sequencing Scheme (BASS) (see, for example, Metzker et al., Nucleic Acids Res 1994, Vol.22, No.20; p. 4259–4267). BASS is a method involving the incorporation of nucleotide analogues which have been modified so as to comprise a blocking group which terminates DNA synthesis. A primer is annealed to a template bound to a solid support and sequence data obtained by repetitive cycles of incorporation of modified nucleotides. At each cycle, the incorporated base is identified in situ before being deprotected to remove the blocking group and allow the next cycle of DNA synthesis.

Methods such as BASS rely on the use of nucleotide analogues that possess polymerase enzyme blocking (or terminator) groups at the 3' hydroxyl position of the sugar on the nucleotide. Typically, the blocking group is a combined terminator and label/reporter moiety such that the incorporated nucleotide can be detected while the bulky label or reporter moiety itself fulfils the role of blocking a polymerase from any further DNA synthesis. Conveniently, as the terminator group is also the reporter moiety, a single reaction allows simultaneous removal of both functions thus allowing subsequent DNA synthesis and for incorporation of the next base to be read.

In order to allow subsequent rounds of DNA synthesis, these polymerase enzyme blocking groups are, typically, attached to the nucleotide via a linking group in such a way that they can be removed. However, conventional sequencing strategies require high temperatures of cycling (typically approximately 95° C. or above) which are associated with pH changes in the reaction mixture. Such conditions can cause reactivity of certain chemical bonds. Accordingly, the coupling methods for attaching blocking and labelling groups to nucleotides which have been used to date have focused on using those linking groups which can withstand changes in chemical conditions (such as temperature and pH). For example, the blocking and label groups can be attached via photosensitive linkage groups and thus cleavable by light irradiation (i.e. photochemical means, see, for example, WO 93/05183) or via chemical means.

However, the use of known nucleotide analogues suffers from a number of disadvantages.

Firstly, by attaching the bulky reporter moiety in the 3' position of the nucleotide, the ability of the DNA polymerase to recognise or tolerate the nucleotide is reduced. Currently known nucleotide terminators are incorporated by polymerases with an efficiency which fails to approach 97%. In addition to being poorly incorporated, modified nucleotides may be inactive (i.e. not incorporated), inhibitory (i.e. inhibit DNA synthesis) or may result in an alteration of the polymerase enzyme fidelity.

Secondly, the known methods of removing the terminator groups require repeated insult by reactive chemicals or irradiation which can result in damage to the template DNA strand through reactions such as base transformation, crosslinking, or depurination.

Any one of, or a combination of, these effects will result in a reduced accuracy in the sequence data obtained and, in particular, a decreased signal-to-noise ratio will be found on detection. Moreover, this means that the amount of sequence data that can be obtained from successive rounds of enzyme incorporation and cleavage is limited. For example, if a combined error of approximately 3% in incorporation and cleavage were to accumulate, the result would be that sequence could only be obtained from 5 bases or fewer of the template DNA before the decreased signal to noise ratio made further sequencing impractical.

Accordingly, there is a need for improved nucleotide analogues. Such analogues may have one or more of the following attributes: tolerated by polymerases; stable during the polymerization phase; and blocking groups can be removed efficiently under conditions which minimise damage to the template strand or template-primer complex. Preferably, the improved analogues display more than one of these features and most preferably they display all of these features.

It is thus an object of the invention to provide a nucleotide analogue to which blocking and reporter moieties are attached at separate positions of the nucleotide. It is another object of the invention to provide a nucleotide analogue to which blocking and reporter moieties are attached via linking groups which are enzyme-cleavable groups. Such latter nucleotide analogues are most suitable for using in sequencing reactions which involve an isothermic reaction and therefore do not involve exposure of the nucleotide analogues to high temperatures and to undesirable variations in chemical conditions. Under the conditions of suitable sequencing reactions, including array-based sequencing technologies (such as BASS), enzyme-cleavable groups will be essentially stable. The use of enzyme-cleavable linking groups removes the need for harsh, template-damaging treatments to remove the blocking and reporter moieties.

DESCRIPTION OF THE INVENTION

The present invention describes the separation of blocking and reporter moieties on a nucleotide and the use of linkage groups cleavable by enzymatic action to attach blocking and reporter moieties to nucleotides.

Accordingly, in a first aspect, the invention provides a nucleotide comprising a reporter moiety and a polymerase enzyme blocking moiety characterised in that the reporter moiety does not also act as a polymerase enzyme blocking moiety.

In a second aspect, the invention provides a compound of Formula I:

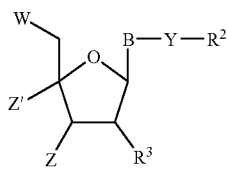
(I)

wherein
  W is a phosphate group
  B is a base
  Y is a linker comprising an enzyme-cleavable group
  $R^2$ is a reporter moiety
  $R^3$ is selected from H or OH
  Z and Z' are selected from H, OH, or a group X—$R^1$, wherein X is a linker comprising an enzyme-cleavable group and $R^1$ is a polymerase enzyme blocking group, provided that at least one of Z and Z' is X—$R^1$.

Suitably, W represents a phosphate group and may be a mono-, di- or tri-phosphate group. In a particularly preferred embodiment W is a triphosphate.

Suitable bases, B, include purines or pyrimidines and, in particular, any of the bases A, C, G, U and T or their analogues.

Suitably, only one of Z and Z' is X—$R^1$. In one preferred embodiment, Z is X—$R^1$ and Z' is H or OH.

In a preferred embodiment, X and/or Y may be a chain of up to 30 bond lengths and may include atoms selected from carbon, nitrogen, oxygen and sulphur atoms, the linker group may be rigid or flexible, unsaturated or saturated as is well known in the field. X and/or Y may further incorporate one or more amino acids joined by peptide bonds. The incorporation of amino acids can be through the incorporation of amino acid monomers or oligomers using standard amino acid chemistry (see, for example, "Synthetic Peptides—A Users Guide" Ed. G. A. Grant; 1992). Suitably, linker Y links the base, B to the reporter moiety $R^2$.

Suitable enzyme-cleavable groups in X and Y include any chemical structure which is recognisable by an enzyme and which, in an enzyme-cleavage reaction, results in the polymerase enzyme blocking group ($R^1$) and/or the reporter moiety ($R^2$) being detached from the compound. The enzyme-cleavable groups in X and Y can be the same or different. In one embodiment, X and/or Y incorporate amino linkage groups.

In a preferred embodiment, where Z is X—$R^1$, the enzyme-cleavage reaction results in the formation of an —OH group in the 3' position thus leaving the incorporated nucleotide capable of binding to a subsequent nucleotide.

In another embodiment, where Z' is X—$R^1$, the enzyme-cleavage reaction leaves a group in the 4' position which allows subsequent incorporation of a nucleotide (i.e. chain extension). In a particularly preferred embodiment, the enzyme cleavage reaction leaves an amino methyl group in the 4' position.

In a particularly preferred embodiment, X and Y comprise the same enzyme-cleavable group thus facilitating a single addition or reaction causing cleavage of both blocking and reporter groups in one reaction.

In a preferred embodiment, the ezyme-cleavable groups may be, for example, groups cleavable by enzymes such as esterases, phosphatases, peptidases (i.e. endo or exo peptidases), amidases, glucosidases or phosphorylases. Suitable enzymes are those that are reactive under mild conditions. (see Handbook of Proteolytic Enzymes, Barrett et al., ISBN 0-12-079370-9). In a particularly preferred embodiment, the enzyme-cleavable group is cleavable by penicillin amidase.

Esterases catalyse the general reaction set out below in Reaction Scheme 1:

Reaction Scheme 1

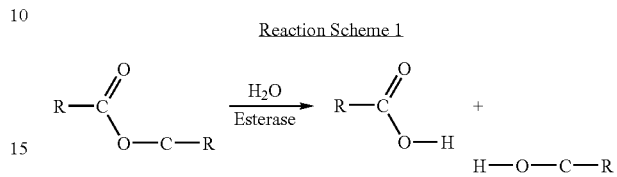

Thus, in a further preferred embodiment of the second aspect, at least one of X and Y comprise a carboxyl group.

Non-specific esterase activity is associated with a number of enzyme systems. This activity has been associated with both physiological function and drug metabolism. Such a non-specific carboxylesterase activity can be used to modify molecules in vitro. Thus in a preferred embodiment, once the nucleotides are incorporated, the linkage groups may be digested with a non-specific esterase to remove the blocking group and reporter moiety without damaging the template strand or the template/primer complex. Following deprotection, DNA synthesis is reinitiated leading to the next cycle of labelled analogue addition.

Other suitable enzyme-cleavable groups include those cleavable by amidases and peptidases.

Amidases catalyse the cleavage of amide bonds as set out in Reaction Scheme 2.

Reaction Scheme 2

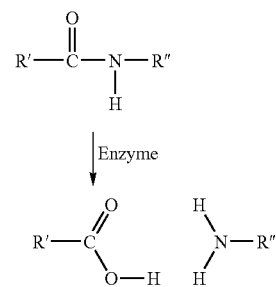

Where R' and R" both represent one or more amino acid residues, then peptidases catalyse the following general reaction set out in Reaction Scheme 3:

Reaction Scheme 3

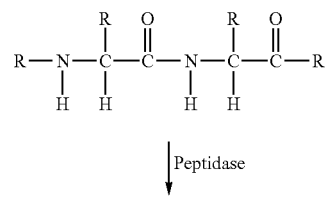

↓ Peptidase

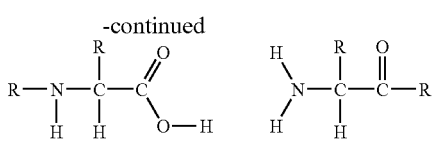

Penicillin amidase (also known as penicillin aminohydrolase; EC 3.5.1.11) cleaves the group:

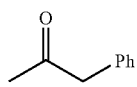

In addition, cleavage of phenylacetic acid by penicillin amidase has been described in WO 97/20855. Accordingly, in a particularly preferred embodiment, X and/or Y comprise a penicillin amidase cleavage site.

Suitable methods for attaching a linker comprising an enzyme cleavable group to a base moiety are described, for example, in Cavallaro et al. Bioconjugate Chem. 2001, 12, 143–151. Further methods are described in Langer et al, Proc Natl Acad Sci USA, 1981, 78, 6633–6637; Livak et al, Nucleic Acids Res, 1992, 20, 4831–4837 and Gebeyehu et al, Nucleic Acids Res, 1987, 15, 4513–4534.

A suitable reporter moiety, $R^2$, may be any one of various known reporting systems. It may be a radioisotope by means of which the nucleoside analogue is rendered easily detectable, for example $^{32}P$, $^{33}P$, $^{35}S$ incorporated in a phosphate or thiophosphate or H phosphonate group or alternatively $^3H$ or $^{14}C$ or an iodine isotope. It may be an isotope detectable by mass spectrometry or NMR. It may be a signal moiety e.g. an enzyme, hapten, fluorophore, chromophore, chemiluminescent group, Raman label, electrochemical label, or signal compound adapted for detection by mass spectrometry.

In a preferred embodiment, the reporter moiety has fluorescent properties and can be detected using a sensitive fluorescence detector. It may be a fluorophore, for example, selected from fluoresceins, rhodamines, coumarins, BODIPY™ dyes, cyanine dyes and squarate dyes (described, for example, in WO 97/40104). Most preferably, the reporter moiety is a cyanine dye. The Cyanine dyes (sometimes referred to as "Cy dyes™"), described, for example, in U.S. Pat. No. 5,268,486, is a series of biologically compatible fluorophores which are characterised by high fluorescence emission, environmental stability and a range of emission wavelengths extending into the near infra-red which can be selected by varying the internal molecular skeleton of the fluorophore.

The reporter moiety may comprise a signal moiety and a linker group joining it to the remainder of the molecule, which linker group may be a chain of up to 30 bond lengths and may include atoms selected from carbon, nitrogen, oxygen and sulphur atoms, the linker group may be rigid or flexible, unsaturated or saturated as is well known in the field.

In a preferred embodiment, different reporter moieties will be chosen such that more than one base can be incorporated and detected in a single sequencing reaction. In a particularly preferred embodiment, each base will be labelled with a different reporter moiety so that all four bases can be used at the same time in a sequencing reaction. The different reporter moieties will enable the different bases to be distinguishable by fluorescence spectroscopy or other optical means. In a preferred embodiment, the reporter moiety is chosen such that 4 distinguishable moieties can be used to label each of the 4 natural bases, A, G, C and T or their analogues such that each of the nucleotides are distinguishable from each other.

Suitably $R^3$ is selected from H or OH. Thus ribonucleotides and deoxyribonucleotides are envisaged together with other nucleoside analogues.

A polymerase enzyme blocking group, $R^1$, is one which should have the functional properties of blocking further elongation of the polymer once the nucleotide of the present invention has been incorporated by a selected polymerase in selected polymerase enzyme conditions. In particular, a blocking group is any chemical group which can be attached to a nucleotide and which will allow the 5' end of the modified nucleotide to attach to a 3' end of another nucleotide in a DNA chain but will not allow attachment of a nucleotide to the 3'hydroxyl group of the modified nucleotide. Suitably, the absence of an OH group in the 3' position will prevent further elongation by polymerase activity. In a particularly preferred embodiment, the blocking group, $R^1$ is selected from acetyl, $CH_3$, glycyl, leucyl and alanyl groups. In another embodiment, the blocking group may be in the form of a di or tri peptide.

In another embodiment, the polymerase enzyme blocking group can be attached at the 4' position i.e. Z' is X—$R^1$. It is postulated that modification at this position results in an analogue that is more readily accepted as a substrate by polymerases. Methods for synthesising nucleotide analogues having a 4' blocking modification are described by Giese et al. in EP 0,799,834.

Where Z' is X—$R^1$, Z is, preferably, OH. In this preferred embodiment, it is speculated that the presence of a 3' OH group in the modified nucleotide of Formula I may facilitate polymerase recognition of the modified analogue and would also leave the nucleotide ready for subsequent incorporation upon detaching blocking group, $R^1$.

Preferably, the blocking group $R^1$ does not also act as a reporter molecule.

In another preferred embodiment, the modified nucleotide remains compatible with elongation enzymology, i.e. it can still be incorporated by a polymerase. Procedures for selecting suitable nucleotide and polymerase combinations will be readily adapted from Metzker et al, Nucleic Acids Res 1994, Vol. 22, No. 20, 4259–4267. In particular, it is desired that a selected polymerase be capable of selectively incorporating a nucleotide.

Examples of particularly preferred compounds of Formula I, in which $R^2$ is the cyanine dye Cy3, include 5-{[N-(carboxypentyl)-trimethinecyanine]amidoacetic acid-3-allyl ester}-3'-acetoxy-2'-deoxyuridine-5'-triphosphate, 5-{[N-(carboxypentyl)-trimethinecyanine]amidoacetic acid-3-allyl ester}-3'-acetoxy-2'-deoxycytidine-5'-triphosphate, 7-{[N-(carboxypentyl)-trimethinecyanine]amidoacetic acid-3-allyl ester}-3'-acetoxy-2'-deoxy-7-deazaadenosine-5'-triphosphate and 7-{[N-(carboxypentyl)-trimethinecyanine] amidoacetic acid-3-allyl ester}-3'-acetoxy-2'-deoxy-7-deazaguanosine-5'-triphosphate. These preferred compounds are shown in FIG. 2. A further preferred compound is 5-[N-Fluorescein-5(and-6) carboxamidohexanoyl] propargylamino-4'-C-(acetylaminomethyl)-2'-deoxyuridine triphosphate (shown in FIG. 6).

In a third aspect of the invention, there is provided a chemical intermediate selected from the group consisting of: 4'-C-(Glycylaminomethyl)thymidine triphosphate; 4'-C-(N-trifluoroacetylaminomethyl)thymidine triphosphate; 4'-C-(Aminomethyl)thymidine triphosphate (shown in FIG. 3);

5-(N-Trifluoroacetyl)propargylamino-4'-C-(acetylaminomethyl)-2'-deoxyuridine; 4'-C-(N-Acetylglycylaminomethyl)thymidine; 4'-C-(N-Leucylaminomethyl)thymidine (shown in FIG. 7); 4'-C-(N-Glycylaminomethyl)thymidine (shown in FIG. 8); N-{α-[4'-methyloxythymidyl] phenyl}phenylacetamide triphosphate (shown in FIG. 9); N-[α-(3'-O-thymidyl)-phenyl)]-phenylacetamide triphosphate, N-{α-[3'-O-(5-N-(α-methyloxy-N'-trifluoroacetylaminopropyl benzamide) phenylacetamide-2'-deoxyuridyl]-phenyl}-phenylacetamide (shown in FIG. 11) and a compound of the following formula:

(42)

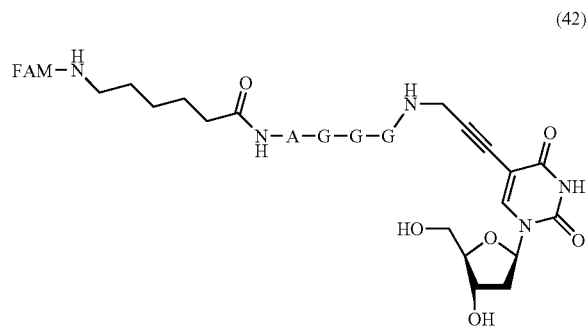

In another aspect of the invention, there is provided a process for the manufacture of a compound in accordance with any of the first, second or third aspects. In a further aspect there is provided a process for the manufacture of a compound of Formula I using an intermediate compound as defined in the third aspect.

In a fourth aspect of the invention, there is provided, a set of nucleotides characterised in that the set contains at least one compound of Formula I. Preferably, such a set will comprise each of the four natural bases A, G, C and T (or their analogues) wherein at least one is a compound of Formula I.

In a preferred embodiment of the fourth aspect the set of nucleotides will comprise at least two compounds of Formula I having different bases, B, characterised in that each compound of Formula I has a different reporter moiety, $R^2$. Thus, for example, the set of nucleotides may comprise compounds of Formula I with bases A and G wherein the compound with base, A, has a first reporter moiety ($R^2$) and the compound with base, G, has a second reporter moiety ($R^2$) wherein the first and second reporter molecules are distinguishable from each other.

In another preferred embodiment of the fourth aspect, the set of nucleotides comprises four compounds of Formula I characterised in that each compound has a different base, B, such that each of the bases A, G, C and T are present and each of the four compounds of Formula I has a reporter moiety which is distinguishable from all of the other three bases.

In a fifth aspect of the invention there is provided, a method for nucleic acid molecule sequencing comprising the steps of
a) immobilising a complex of a primer and a template to a solid phase
b) incubating with a polymerase in the presence of a compound of Formula I.

In one embodiment of the fifth aspect, the complex of primer and template can be preformed by incubation under appropriate hybridisation conditions before immobilising the complex onto a solid phase. In another embodiment, the primer or the template can be immobilised onto a solid phase prior to formation of the complex by introduction of the appropriate hybridisation partner (i.e. template or primer, respectively). In yet another embodiment, the complex immobilised onto the solid phase can be a single nucleic acid molecule comprising both "primer" and "template"; for example, the immobilised nucleotide can be a hairpin structure.

Suitable polymerases are enzymes that perform template-dependent base addition including DNA polymerases, reverse transcriptases and RNA polymerases. Suitable native or engineered polymerases include but are not limited to T7 polymerase, the Klenow fragment of E. coli polymerase which lacks 3'-5'exonuclease activity, E. coli polymerase III, Sequenase™, φ29 DNA polymerase, exonuclease-free Pfu, exonuclease-free Vent™ polymerase, Thermosequenase, Thermosequenase II, Tth DNA polymerase, Tts DNA polymerase, MuLv Reverse transcriptase or HIV reverse transcriptase. The selection of an appropriate polymerase depends on the interaction between a polymerase and the specific modified nucleotide (as described by Metzker et al., Nucleic Acids Res 1994, Vol.22, No.20; p. 4259–4267).

Nucleotides comprising enzyme-cleavable linkage groups such as carboxyl ester attachment groups are suitable for use in sequencing reactions used in array based sequencing, such as BASS. Such reactions are isothermic, unlike cycle sequencing, so allowing much better control of reaction conditions. In particular, the sequencing reaction takes place at relatively low temperatures (typically less than 70° C.) thus enabling enzyme-cleavable linkage groups, such as the carboxyl ester attachment, to remain stable under these sequencing reaction conditions. Accordingly, polymerases which may be useful in the fifth aspect of the invention include thermostable polymerases and non-thermostable polymerases.

In a preferred embodiment of the fifth aspect, the method further comprises the steps of
c) detecting the incorporation of a compound of Formula I
d) incubating in the presence of enzyme under suitable conditions for enzymatic cleavage of the enzyme-cleavable groups X and Y Suitable conditions for enzyme cleavage of the enzyme-cleavable groups will depend on the nature of the enzymes involved. Enzyes such as carboxyesterases are active under a broad range of conditions and do not require co-factors. Commercially available carboxyesterases will hydrolyse esters under mild pH conditions of between pH 7.0 and pH 8.0. e.g. 0.1M NaCl, 0.05M Tris.HCl, pH 7.5. Suitable conditions for cleavage by amidases and peptidases are exemplified in Example 8 below.

In another embodiment of the fifth aspect, the method further comprises
e) repeating steps a)–d)

In a preferred embodiment of the fifth aspect, the enzyme in step d) is an amidase.

In a further aspect of the invention there is provided use of a compound of Formula I in a sequencing reaction.

Briefly, sequencing reactions using modified nucleotides in accordance with the first aspect of the invention may be performed as follows. Primer template complexes are immobilised to a solid surface and contacted with modified nucleotides in the presence of a suitable buffer also containing a polymerase, such as Klenow fragment of E. coli polymerase which lacks 3'-5'exonuclease activity, and a commercially available pyrophosphatase. The reaction is incubated under suitable conditions for a polymerase-mediated base addition reaction followed by the removal of non-incorporated nucleotides and enzymes by washing with a wash buffer. Suitably, the wash buffer contains a buffering agent, such as an organic salt, to maintain a stable pH of approximately pH 6 to pH 9 and possibly also comprises monovalent or divalent cations and a detergent so as to eliminate non-covalently bound molecules from the solid surface. Where the modified nucleotides comprise a fluorescent reporter molecule, incorporated nucleotides are detected by measuring fluorescence and the corresponding nucleotide identified. Following identification, the templates are contacted with a buffered solution containing an excess of a protein displaying the appropriate enzyme activity and incubated under conditions for enzyme cleavage activity. For example, where the enzyme-cleavable group linking reporter molecule and/or blocking group to the nucleotides is a carboxyl group, the solution contains an excess of a protein displaying non-specific esterase activity. Following enzyme activity, the products of enzymatic cleavage are eliminated by washing as above. Following the washing step, the immobilised template is washed with an excess of buffer used for the polymerase reaction and the steps of polymerase-mediated base addition, detection of incorporated nucleotide and enzyme-cleavage activity are repeated to obtain further sequence data.

SPECIFIC DESCRIPTION

For the purposes of clarity, certain embodiments of the present invention will now be described by way of example with reference to the following figures.

EXAMPLE 1

Figure 1:
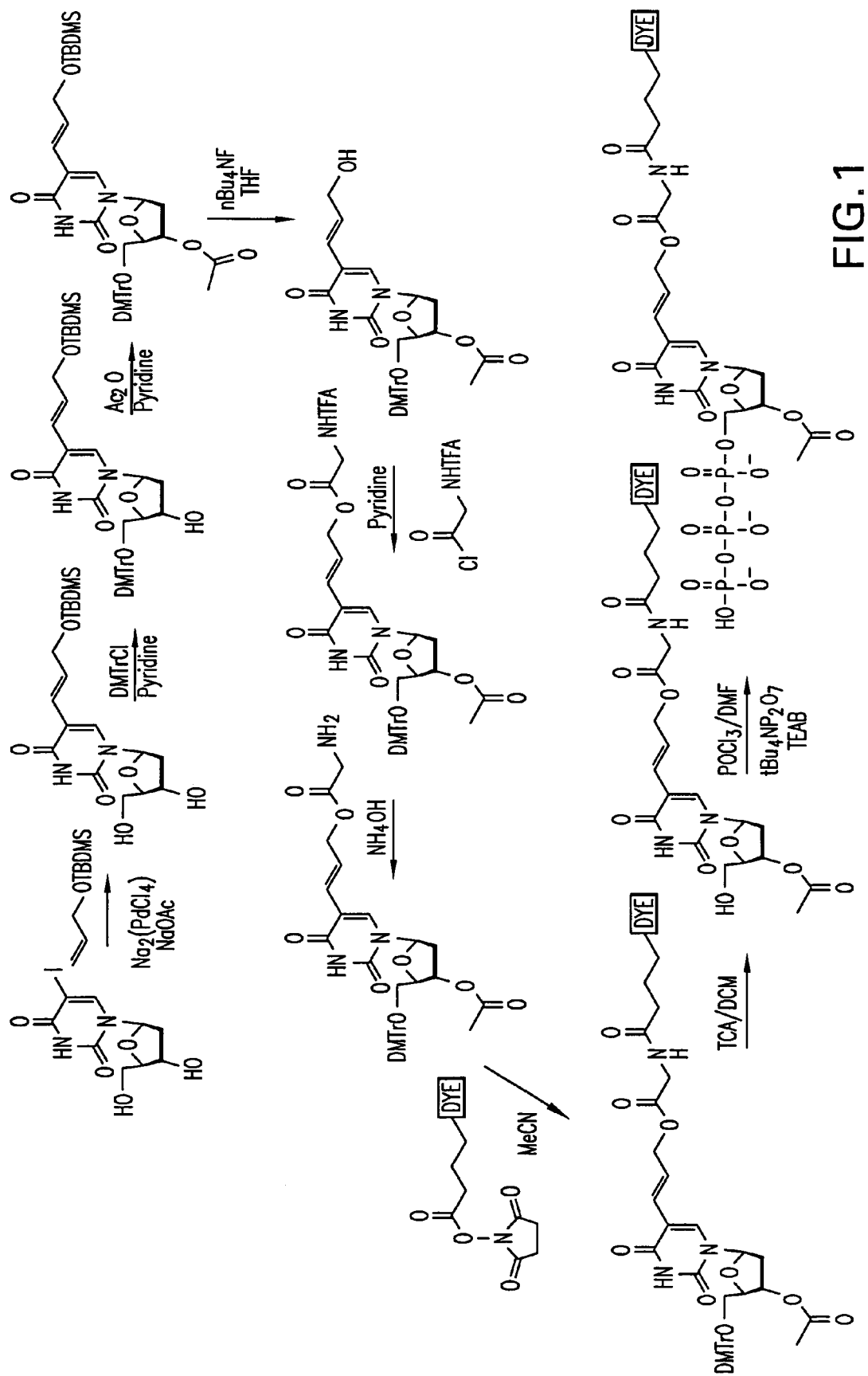
FIG. 1 shows a reaction scheme for syntesising a compound of Formula I.
Figure 2:
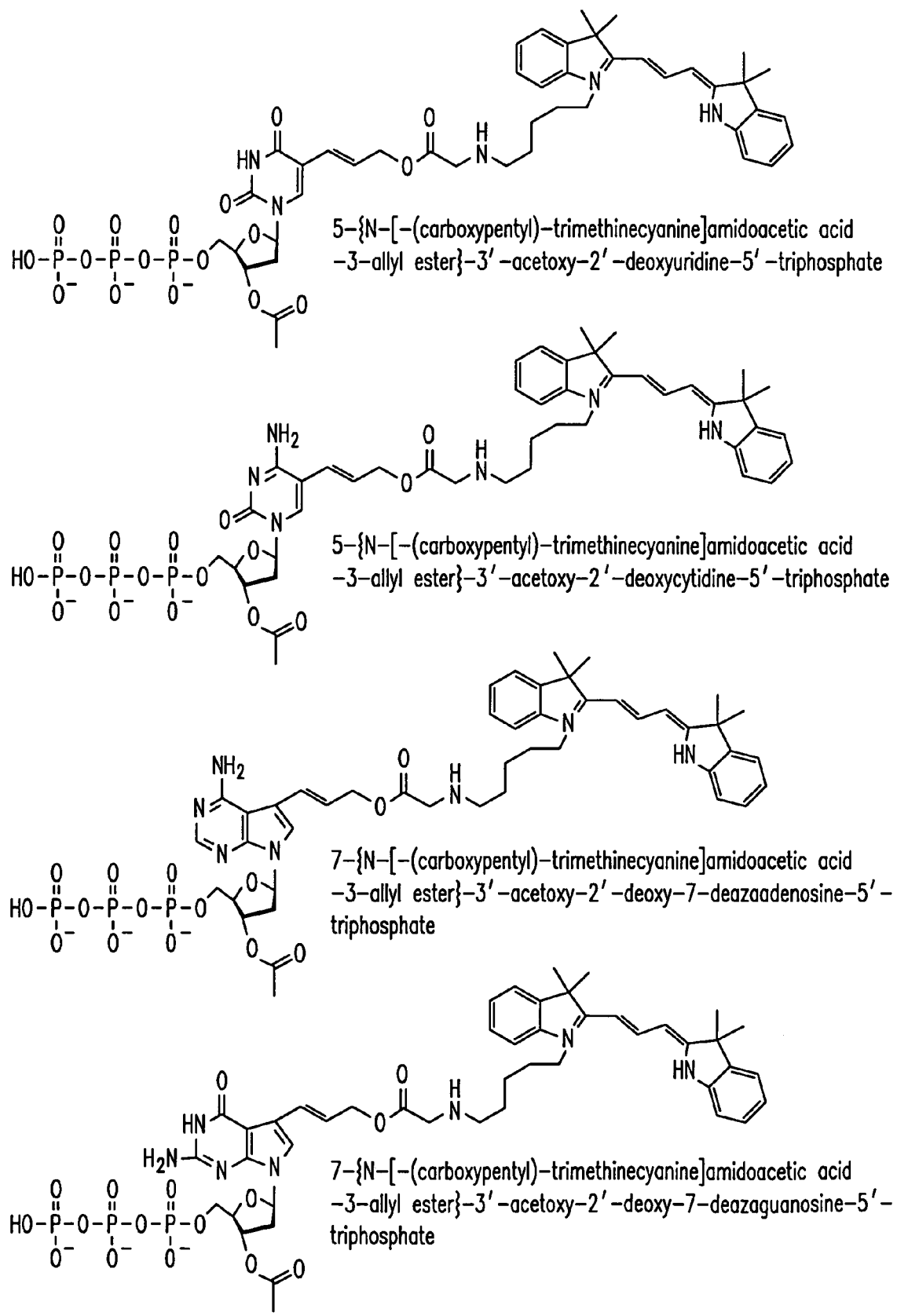
FIG. 2 shows examples of compounds of Formula I.

A reaction scheme for the synthesis of an example of a compound of Formula I is set out in FIG. 1 using 5-iodo-2'-deoxyuridine (Sigma-Aldrich Chemical Co.) as the starting material and incorporating the dye, Cy3, by reaction with (N-hydroxy)succinimide Cy3 ester.

In the reaction scheme, the following abbreviations are used: TBDMS—tertbutyldimethylsilyl; DMTr—Dimethoxytrityl; TFA—trifluoroacyl; nBu—linear Butyl chain; MeCN—Acetonitrile; TCA—Trichloroacetic acid; DCM—Dichloromethane; DMF—N,N-Dimethylformamide; TEAB—Tetraethylammonium bicarbonate buffer; THF—Tetrahydrofuran; Ac—Acetyl.

Wherein TBDMS, Ac, TFA and nBu have the following structural formulae:

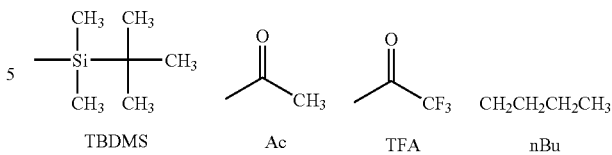

EXAMPLE 2

Synthesis of Nucleotides with a 4' Groups (4'-C(Glycylaminomethyl)thymidine triphosphate (6), 4'-C-(N-trifluoroacetylaminomethyl)thymidine triphosphate (8) and 4'-C-(Aminomethyl)thymidine triphosphate (9)).

Figure 3:
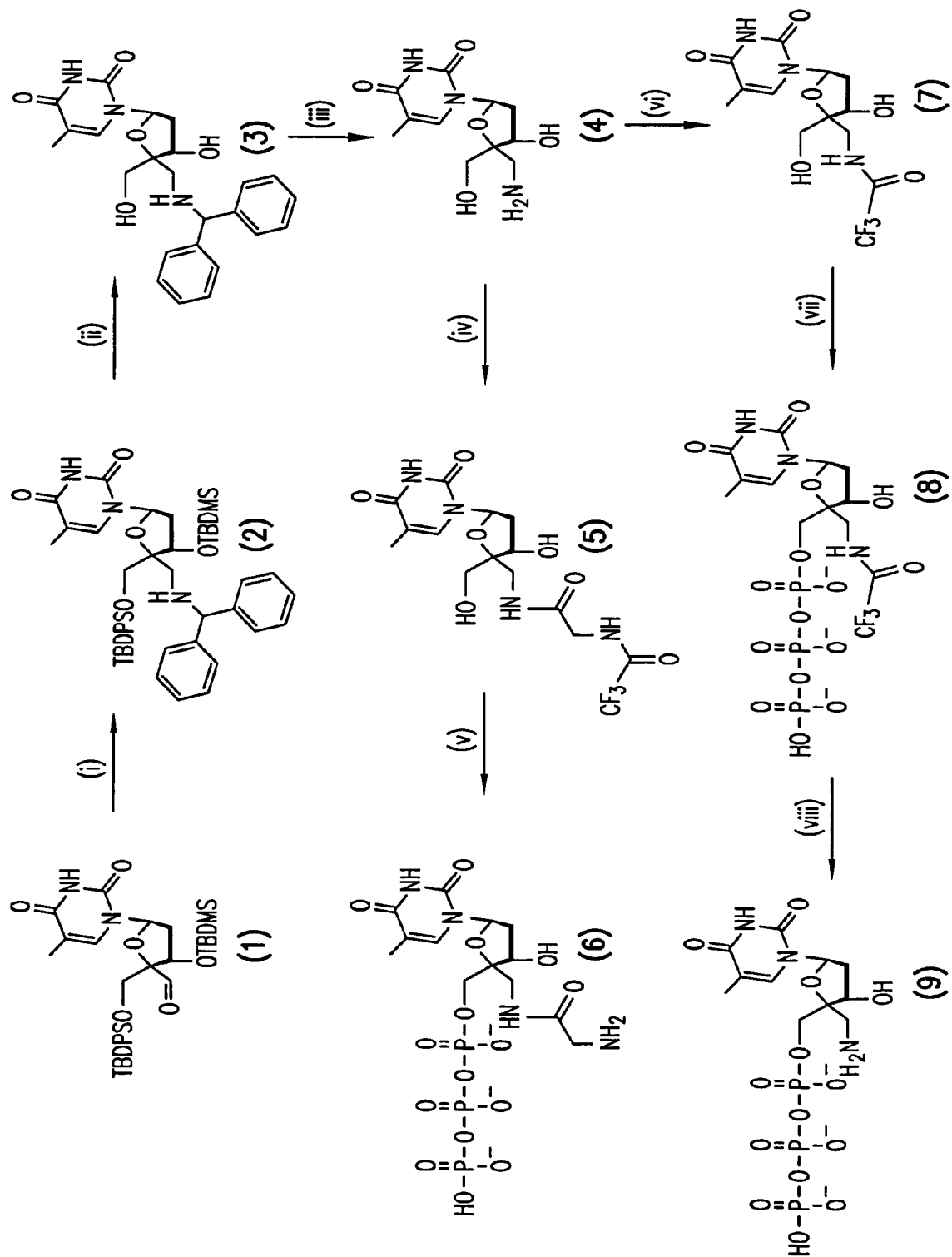
FIG. 3 shows a reaction scheme for synthesising nucleotide analogues.

FIG. 3 illustrates the synthetic pathway for nucleotide analogues indicated as (6), (8) and (9) via the intermediate compound (4).

i) 3'-O-[(tertbutyl)dimethylsilyl]-5'-O-[(tertbutyl)diphenylsilyl]-4'-C-(1,1'-diphenylmethylaminomethyl)thymidine (2).

The starting material 3'-O-[(tertbutyl)dimethylsilyl]-5'-O-[(tertbutyl)diphenylsilyl]-4'-C-formylthymidine (1) (described in Marx et al. Helv. Chim. Acta. 1996, 79, 1980–1994 and references cited therein.) (1.7 g, 2.7 mmol) and $Ph_2CHNH_2$ (0.53 g, 2.9 mmol; 0.5 mL) were dissolved in anhydrous acetonitrile (10 mL) at ambient temperature. Neat glacial acetic acid (0.11 g, 1.9 mmol, 0.11 mL) was then added and the solution stirred for 30 minutes at ambient temperature, during which time a white precipitate formed. Solid $NaBH_3CN$ (0.25 g, 4.1 mmol) was then added in portions to the stirred suspension. The resulting mixture was then stirred at ambient temperature for 18 hours. The solvent was then removed under vacuum and the residue redissolved in dichloromethane and washed with brine. The organic layer was then separated, dried over $MgSO_4$ and then filtered. Concentration of the filtrate under vacuum gave a white foam which was purified by flash column chromatography (7:3, dichloromethane:ethyl acetate) to afford the title compound (2) (1.2 g, 55%) as a white foam. $\delta_H$(300 MHz, $CDCl_3$) 8.3(1H, s, br, $N^3$—H), 7.72–7.65(4H, dd, Ph), 7.49–7.14(17H, m, Ph$_2$CHNH, Ph$_2$SitBu; H-6, s, obs), 6.37 (1H, dd, H-1'), 4.67(1H, s, Ph$_2$CHNH), 4.57(1H, dd, H-3'), 3.96(2H, 2d, H-5'), 2.70(1H, d, 4'-C—$CH_2$), 2.55(1H, d, 4'-C—$CH_2$), 2.25(2H, m, H-2'), 1.61(3H, s, 5-$CH_3$), 1.11 (9H, s, tBuSiPh$_2$), 0.75(9H, s, tBuSiMe$_2$), 0.11(3H, s, MeSi), 0.01(3H, s, MeSi); $\delta_C$(75.45 MHz, $CDCl_3$) 163.47, 150.13, 144.14, 143.79, 135.72, 135.65, 133.07, 132.58, 130.14, 129.63, 128.67, 128.59, 128.41, 127.97, 126.94, 126.88, 111.03, 89.79, 83.84, 72.89, 67.99, 66.74, 49.80, 41.85, 27.08, 25.63, 19.44, 17.85, 14.20, 12.07, −4.68, −5.36; $\nu$ cm$^{-1}$ 1688, 1112, 833.

ii) 4'-C-(1,1'-diphenylmethylaminomethyl)thymidine (3).

3'-O-[(tertbutyl)dimethylsilyl]-5'-O-[(tertbutyl)diphenylsilyl]-4'-C-(1,1'-diphenylmethylaminomethyl)thymidine (2) (1.2 g, 1.5 mmol) was dissolved in tetrahydrofuran (50 mL) at ambient temperature. A solution of tetrabutylammonium fluoride in tetrahydrofuran (4.5 mL) was then added to the solution. The resulting mixture was stirred for 3 hours at ambient temperature. Methanol (5 mL) was then added and the reaction mixture concentrated under vacuum. The residue was purified by flash column chromatography (95:5 dichloromethane:methanol) to give the title compound (3) as an amorphous white solid (0.65 g, 100%) on removal of solvent from the appropriate fractions. $\delta_H$(300 MHz, $d_6$-DMSO) 11.23(1H, s, br, $N^3$—H), 7.75(1H, s, H-6), 7.41–7.15(10H, m, Ph$_2$CHNH), 6.21(1H, dd, H-1'), 5.57 (1H, d, br, 3'-OH), 5.21(1H, t, 5'-OH), 4.78(1H, s, Ph$_2$CHNH), 4.35(1H, m, H-3'), 3.61(2H, 2d, H-5'), 2.54(2H, 2d, 4'-C—CH$_2$), 2.18(2H, m, H-2'), 1.75(3H, s, 5-CH$_3$); $\delta_C$(75.45 MHz, $d_6$-DMSO) 150.46, 144.53, 144.28, 136.28, 128.36, 126.99, 126.74, 109.17, 88.39, 83.18, 66.79, 64.10, 54.91, 12.27.

iii) 4'-C-Aminomethylthymidine (4).

4'-C-(1,1'-diphenylmethylaminomethyl)thymidine (3) (0.65 g, 1.5 mmol) was dissolved in absolute ethanol (50 mL). Cyctohexene (12 mL), glacial acetic acid (5 mL) and 5%-palladium on charcoal (0.6 g) were added and the mixture heated under reflux with stirring. The solution was heated for 5 hours and then allowed to cool to ambient temperature. Palladium catalyst was removed by filtration through celite and the filtrate was concentrated under vacuum to give the crude title compound (4), which was used in the following step without further purification. ES +ve m/z 272(M+H)$^+$, 242(M—CH$_2$NH$_2$)$^+$. For an alternative synthesis of this compound see: Wang et al; *Tetrahedron Letters* 1996, 37, 6515–6518.

iv) 4'-C-(N-trifluoroacetylglycylaminomethyl)thymidine (5).

4'-C-Aminomethylthymidine (4) (0.14 mmol) was dissolved in anhydrous N,N-dimethylformamide (1 mL). N-Trifluoroacetylglycine (0.036 g, 0.21 mmol) and O-(N-succimidyl)-N,N,N',N'-tetramethyluronium tetrafluoroborate [TSTU] (0.085, 0.28 mmol) were then added and the solution stirred at ambient temperature. Diisopropylethylamine (0.036 g, 0.28 mmol, 0.05 mL) was then added dropwise to the solution with stirring. After 12 hours the solvent was removed under vacuum and the residue redissolved in dichloromethane:methanol (9:1). Applied solution directly to a silica gel column and eluted with dichloromethane:methanol (9:1). Fractions containing the desired material were pooled and the solvent removed under vacuum to give the title compound (5) as a clear, glassy material (0.28 g, 28% from crude 4). $\delta_H$(300 MHz, CD$_3$OD) 7.91(1H, s, H-6), 6.27(1H, dd, H-1'), 4.49(1H, dd, H-3'), 3.74(2H, s, glycyl CH$_2$), 3.52(1H, d, H-5'), 3.51(2H, s, 4'-C—CH$_2$), 3.43(1H, d, H-5'), 2.32(2H, m, H-2'), 1.68(3H, s, 5-CH$_3$); ES +ve m/z 425(M+H)$^+$, 442(M+H$_2$O)$^+$, 447(M+Na)$^+$.

v) 4'-C-(Glycylaminomethyl)thymidine triphosphate (6).

4'-C-(N-trifluoroacetylglycylaminomethyl)thymidine (5) (0.026 g, 0.06 mmol) and proton sponge (0.02 g, 0.09 mmol) were dissolved in trimethylphosphate (1 mL) at ambient temperature. The solution was then cooled to 0 C. on an ice bath under an atmosphere of nitrogen. Phosphorous oxychloride (0.02 g, 0.12 mmol, 0.01 mL) was then added dropwise to the cooled mixture while stirring. After stirring for two hours at 0 C. a solution of 0.5M tri-n-butylammonium pyrophosphate in N,N-dimethylformamide (1 mL) and tributylamine (0.075 mL) was added to the cooled solution. After stirring for a further two minutes 0.2M trimethylammonium bicarbonate buffer (2 mL) was added and the solution allowed to warm to ambient temperature. The solution was stirred for 45 minutes at ambient temperature and then concentrated under vacuum. The oily residue was then redissolved in concentrated ammonia solution (1 mL) and allowed to stand overnight at ambient temperature. Removal of the solvent under vacuum then gave an oily residue which was redissolved in distilled water and subjected to purification by ion exchange chromatography (DEAE Sephacryl, eluted with 0–100% water—0.8M triethylammonium bicarbonate buffer). Fractions containing the desired product were detected by U.V. and pooled. Lyophilisation of the appropriate fractions gave a white residue which was redissolved in water and eluted through a preparative C18 hplc column with water. Fractions containing the desired product were pooled and lyophilised to give the title compound (6) as a white foam (0.8 μmol, 13%). $\delta_H$(300 MHz, D$_2$O) 7.48(1H, s, H-6), 6.19(1H, dd, H-1'), 3.99(3H, dd, H-3',m, br, H-5'), 3.50(1H, d, 4'-C—CH$_2$), 3.38(2H, s, glycyl CH$_2$), 3.36(1H, d, 4'-C—CH$_2$), 2.36(2H, m, H-2'), 1.77(3H, s, 5-CH$_3$); $\delta_P$(121.5 MHz, D$_2$O) –5.6(d), –10.8(d), –19.0(t); $\lambda_{max}$ 264 nm.

vi) 4'-C-(N-trifluoroacetylaminomethyl)thymidine (7).

4'-C-Aminomethylthymidine (4) (1.5 mmol) was dissolved in methanol (10 mL) and triethylamine (1.5 mL) at ambient temperature. The solution was then treated with neat ethyl trifluoroacetate (1 mL) and the resulting solution stirred for 18 hours at ambient temperature with exclusion of moisture. The solvents and reagents were then removed under vacuum to give the crude product. Purification by flash column chromatography (9:1 dichloromethane:methanol) afforded the title compound (7) as a white foam (0.37 g, 66%). $\delta_H$(300 MHz, CD$_3$OD) 8.77(1H, t, br, $N^3$—H), 7.73(1H, s, H-6), 6.24(1H, dd, H-1'), 4.56(1H, dd, H-3'), 3.6(3H, s, H-5', obs d, 4'-C—CH$_2$), 3.53(1H, d, 4'-C—CH$_2$), 2.35(2H, m, H-2'), 1.81(3H, s, 5-CH$_3$); $\delta_C$(75.45 MHz, CD$_3$OD), 166.24, 160.08–158.62(q, CF$_3$CO), 152.21, 138.11, 123.01–111.51(q, CF$_3$CO), 111.51, 88.93, 85.69, 72.79, 64.23, 41.70, 40.81, 12.40; ES +ve m/z 368 (M+H)$^+$, 390(M+Na)$^+$; ν cm$^{-1}$ 1684. For an alternative synthesis of this compound see Wang et al, *Tetrahedron Letters* 1996, 37, 6515–6518.

vii) 4'-C-(N-trifluoroacetylaminomethyl)thymidine triphosphate(8).

4'-C-(N-trifluoroacetylaminomethyl)thyridine (7) was weighed into a round-bottom flask and the flask flushed with argon. Pyridine and 1,4-dioxane were then added to give a clear solution. A 1M solution of 2-Chlorol-4H-1,3,2-dioxaphosphorin-4-one was then added to the stirred solution. After stirring for 30 minutes a 0.5M solution of tributylammonium pyrophosphate in DMF and tributylamine were added together and the resulting solution stirred for a further 30 minutes. A 1% solution of iodine in pyridine:water 98:2 was then added and the solution stirred for a further 30 minutes. Excess iodine was then destroyed by the addition of saturated sodium thiosulfate solution. The reaction mixture was then concentrated to give a crude product which was then initially purified by the procedure described for the preparation of compound (6). Final purification was achieved using preparative reverse-phase HPLC, eluting with 0.1M triethyammonium bicarbonate:acetonitrile. Obtained the title compound (8) as a white powder after lyophilisation of the appropriate fractions (0.54 mg). $\delta_H$(300 MHz, D2O) 7.45(1H, s, H-6), 6.23(1H, dd, H-1'), 3.76(1H, dd, H-3'), 3.00(2H, 2d, H-5'), 2.61(2H, 2d, 4'-C—CH2), 2.10(2H, m, H-2'), 1.62(3H, s, 5-CH3); $\delta_P$(121.5 MHz, D2O) –4.9(d), –10.5(d), –20.4(t); $\lambda_{max}$ 266 nm.

viii) 4'-C-(Aminomethyl)thymidine triphosphate (9).

4'-C-(N-trifluoroacetylaminomethyl)thymidine triphosphate (8) was dissolved in concentrated aqueous ammonia solution and allowed to stand for 18 hours at ambient temperature. The solution was then lyophilised to give the title compound (9) as a white powder.

EXAMPLE 3

Synthesis of Nucleotide with a 4' Blocking Group and a Fluorescent Label Attached to the Base (5-[N-Fluorescein-5(and-6)carboxamidohexanoyl]propargylamino4'-C-(acetylaminomethyl)-2'-deoxyuridine triphosphate (18)).

Figure 4:
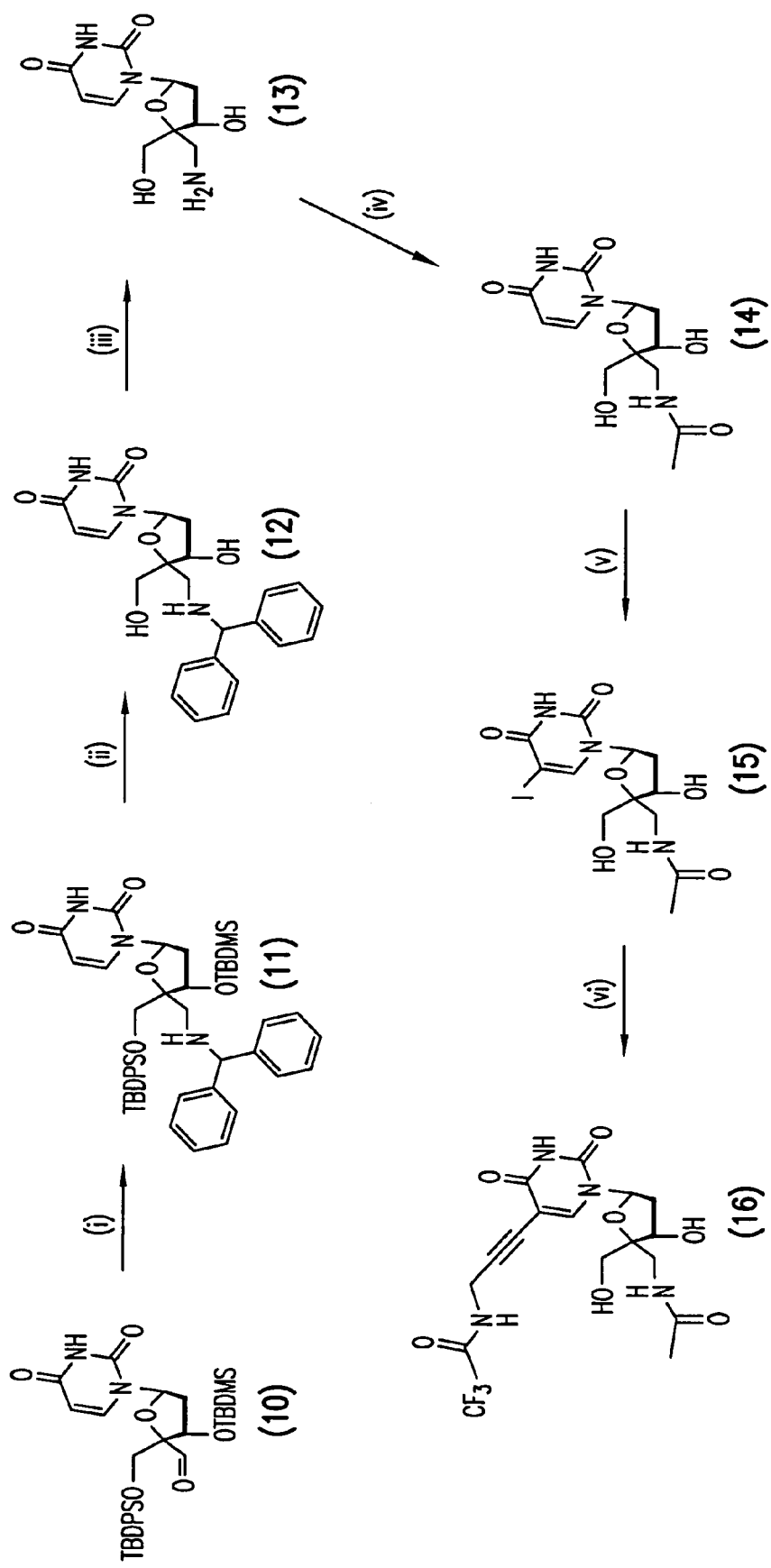
FIGS. 4 and 5 show reaction schemes for synthesising nucleoside analogues.

FIG. 4 illustrates the synthetic pathway for the nucleoside analogue, 5-(N-Trifluoroacetyl)propargylamino-4'-C-(acetylaminomethyl)-2'-deoxyuridine (16).

i) 3'-O-[(tertbutyl)dimethylsilyl]-5'-O-[(tertbutyl)diphenylsilyl]-4'-(1,1'-diphenylmethylaminomethyl)-2'-deoxyuridine (11).

3'-O-[(tertbutyl)dimethylsilyl]-5'-O-[(tertbutyl)diphenylsilyl]-4'-C-formyl-2-deoxyuridine (10) (Yang et al; *Tetrahedron Letters* 1992, 33, 37–40.) (0.15 g, 0.25 mmol) was treated with Ph$_2$CHNH$_2$ (0.07 g, 0.37 mmol, 0.064 mL), glacial acetic acid (0.015 g, 0.26 mmol, 0.015 mL) and NaBH$_3$CN (0.023 g, 0.37 mmol) in acetonitrile (1 mL) according to the procedure used for the preparation of compound (2). The title compound (11) was obtained as clear, viscous oil (0.13 g, 69%). $\delta_H$(300 MHz, CDCl$_3$) 8.02(1H, s, br, N$^3$—H), 7.81(1H, d, H-6), 7.69–7.18(20H, m, Ph$_2$CHNH, tBuSiPh$_2$), 6.32(1H, dd, H-1'), 5.30(1H, d, H-5), 4.67(1H, s, Ph$_2$CHNH), 4.61(1H, dd, H-3'), 4.02(1H, d, H-5'), 3.87(1H, d, H-5'), 2.69(1H, d, 4'-C—CH$_2$), 2.53 (1H, d, 4'-C—CH$_2$), 2.37(1H, m, H-2'), 2.17(1H, m, H-2'), 1.10(9H, s, tBuSiPh$_2$), 0.75(9H, s, tBuSiMe$_2$), 0.01(6H, s, tBuSiMe$_2$); ES +ve m/z 776(M+H)$^+$.

ii) 4'-C-(1,1'-diphenylmethylaminomethyl)-2'-deoxyuridine (12).

3'-O-[(tertbutyl)dimethylsilyl]-5'-O-[(tertbutyl)diphenylsilyl]-4'-C-(1,1'-diphenylmethylaminomethyl)-2'-deoxyuridine (11) (0.13 g, 0.16 mmol) was treated with tetrabutylammonium fluoride solution (0.45 mL) in tetrahydrofuran (5 mL) according to the procedure used for the preparation of compound (3). The title compound (12) was obtained as a clear glass (0.056 g, 78%). $\delta_H$(300 MHz, d$_6$-DMSO) 11.25(1H, s, br, N$^3$—H), 7.90(1H, d, H-6), 7.40–7.15(10H, m, Ph$_2$CHNH), 6.19(1H, dd, H-1'), 5.93(1H, d, br, 3'-OH), 5.91(1H, s, br, Ph$_2$CHNH), 5.11(1H, t, br, 5'-OH), 4.78(1H, s, Ph$_2$CHNH), 4.33(1H, dd, H-3'), 3.61(1H, d, H-5'), 2.52–2.49(2H, m, 4'-C—CH$_2$), 2.18(2H, m, H-2'); $\delta_C$(75.45 MHz, d$_6$-DMSO) 163.13, 150.43, 144.50, 144.25, 140.62, 128.34, 126.97, 126.92, 126.72, 101.60, 88.63, 83.50, 72.0, 66.85, 58.8, 51.15; ES +ve m/z 424(M+H)$^+$.

iii) 4'-C-Aminomethyl-2'-deoxyuridine (13).

4'-C-(1,1'-diphenylmethylaminomethyl)-2'-deoxyuridine (12) (0.056 g, 0.13 mmol) was treated with cyclohexene (1 mL), glacial acetic acid 0.5 mL) and 5% palladium on charcoal (0.06 g) in ethanol (5 mL) according to the procedure used for the preparation of compound (4). The crude product was purified by dissolving in water and washing with toluene. The aqueous layer was separated and the solvent removed under vacuum to give the title compound (13) as an amorphous solid (0.034 g, 100%). $\delta_H$(300 MHz, D$_2$O) 7.64(1H, d, H-6), 6.22(1H, dd, H-1'), 5.72(1H, d, H-5), 4.43(1H, m, H-3'), 3.56(2H, 2d, H-5'), 3.26(1H, d, CH$_2$NH$_2$), 3.05(1H, d, CH$_2$NH$_2$), 2.40(2H, m, H-2'); $\delta_C$(75.45 MHz, D$_2$O) 166.95, 152.46, 142.67, 103.11, 86.77, 86.43, 73.97, 64.82, 41.59, 39.25; ES +ve m/z 258(M+H)$^+$, 242(M–NH$_3$)$^+$.

iv) 4'-C-(Acetylaminomethyl)-2'-deoxyuridine (14)

4'-C-Aminomethyl-2'-deoxyuridine (13) (0.034 g, 0.13 mmol) was dissolved in anhydrous N,N-dimethylformamide (0.5 mL) at ambient temperature. Excess pentafluorophenyl acetate (0.88 g, 0.39 mmol) was then added directly to the reaction mixture as a solid. The resulting solution was stirred for 18 hours at ambient temperature. The solvent was then removed under vacuum and the residue re-dissolved in water and then washed with toluene. The aqueous layer was then separated and the solvent removed under vacuum. The title compound was obtained as an amorphous solid (0.032 g, 82%). $\delta_H$(300 MHz, D$_2$O) 7.68(1H, d, H-6), 6.11(1H, dd, H-1'), 5.71(1H, d, H-5), 4.44(1H, dd, H-3'), 4.49(2H, 2d, H-5'), 3.33(2H, 2d, 4'-C—CH$_2$), 2.33(2H, m, H-2'), 1.89 (3H, s, CH$_3$CONH); $\delta_C$(75.45 MHz, D$_2$O) 175.60, 167.08, 152.43, 142.86, 102.93, 88.93, 85.57, 71.91, 63.16, 40.37, 39.15, 22.72; ES +ve m/z 300(M+H)$^+$, 242(M–CH$_3$CONH)$^+$.

v) 5-Iodo-4'-C-(acetytaminomethyl)-2'-deoxyuridine (15)

Iodine (0.032 g, 0.13 mmol) was dissolved in 1,4-dioxane (1 mL) at ambient temperature. PhI(COCF$_3$) (0.056 g, 0.13 mmol) and pyridine (0.022 g, 0.28 mmol, 0.023 mL) were then added and the reaction mixture stirred until iodine colour faded. 4'-C-(Acetylaminomethyl)-2'-deoxyuridine (14) (0.032, 0.11 mmol) in pyridine (0.25 mL) was then added dropwise to the reaction mixture. The mixture was warmed to 60 C. for on hour and then allowed to cool to ambient temperature after which the solvents were removed under vacuum. The residue was re-dissolved in 9:1 dichloromethane and then eluted through a short flash silica gel column using 9:1 dichloromethane:methanol. The title compound (15) was obtained, with some unreacted starting material, as an amorphous solid. $\delta_H$(300 MHz, CD$_3$OD) 8.52(1H, s, H-6), 6.21(1H, dd, H-1'), 4.48(1H, dd, H-3'), 3.60(2H, 2d, H-5'), 3.39–3.29(2H, 2d, 4'-C—CH$_2$), 2.50–2.24(2H, m, H-2'), 1.98(3H, s, CH$_3$CONH).

vi) 5-(N-Trifluoroacetyl)propargylamino-4'-C-(acetylaminomethyl)-2'-deoxyuridine (16)

5-Iodo-4'-C-(acetylaminomethyl)-2'-deoxyuridine (15) (0.1 mmol) and CuI (0.01 g, 0.05 mmol) were weighed into an round-bottom flask equipped with a magnetic stirrer bar. The flask was then fitted with a septum and flushed with dry argon. N,N-dimethylformamide (0.5 mL) was added to the flask and the contents stirred until all solids were dissolved. A solution of N-(tifluoroacetyl)propargylamine (0.05 g, 0.33 mmol) in triethylamine (0.02 g, 0.22 mmol, 0.03 mL) was then added to the flask and the resulting solution stirred for five minutes. Solid tetrakis(triphenylphosphine) palladium (0.031 g, 0.03 mmol) was then added and the resulting mixture stirred at ambient temperature for 4 hours. The reaction mixture was then diluted with 1:1 dichloromethane:methanol (2 mL) before adding solid sodium hydrogencarbonate. The mixture was stirred for a further hour before filtering through celite. The filtrate was then concentrated under vacuums. The residue was purified by flash column chromatography (95:5 dichloromethane:methanol). Obtained the title compound as an amorphous solid (5.3 mg). $\delta_H$(300 MHz, CD$_3$OD) 8.32(1H, s, H-6), 6.22(1H, dd, H-1'), 4.46(1H, dd, H-3'), 4.26(2H, s, propargyl CH$_2$), 3.59(2H, 2d, H-5'), 3.53(1H, d, 4'-C—CH$_2$), 3.36(1H, d, 4'-C—CH$_2$), 2.37(2H, m, H-2'), 1.97(3H, s, CH$_3$CONH); $\delta_C$(75.45 MHz, CD$_3$OD) 174.33, 164.66, 151.15, 145.79, 124.5–110.8(q, CF$_3$CONH), 99.44, 90.38, 88.35, 86.68, 76.01, 72.66, 64.21, 41.61, 41.24, 22.52, 9.25; ES +ve m/z 470(M+H)$^+$, 493(M+Na)$^+$.

Figure 5:
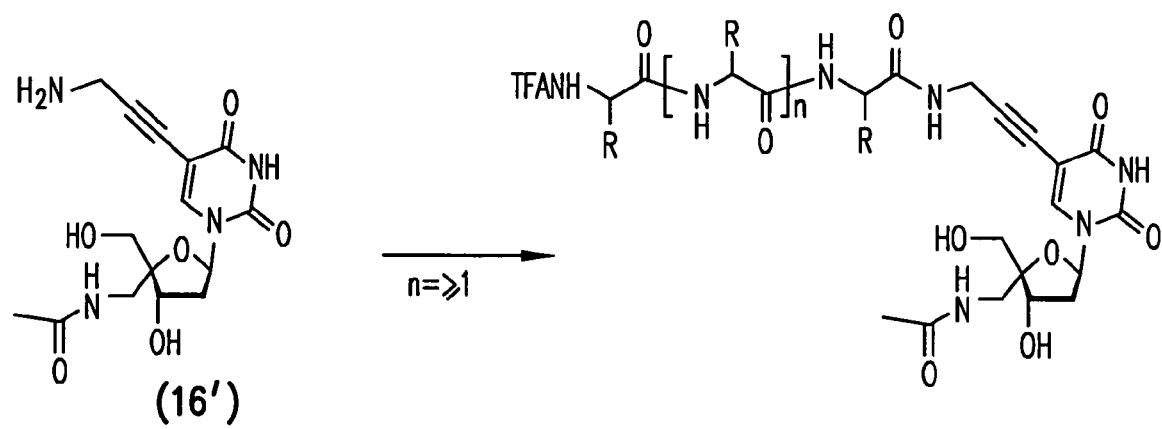

A longer peptidase or amidase cleavable linker is introduced into compound (16') (TFA deprotected analogue of compound (16)) according to the reaction scheme of FIG. 5 in which R is the side chain of any of the natural amino acids.

5-propargylamino-4'-C-(acetylaminomethyl)-2'-deoxyuridine (16') is coupled to suitably derivatised (protected) commercially available peptides (e.g Bachem) using standard peptide coupling reagents (e.g. TSTU, EDCI, DCC, HOBt etc.) or assembled by the sequential addition of suitably derivatised (protected) amino acids following standard peptide synthesis protocols either in solution or on solid phase (see, for example, "Synthetic Peptides—A Users Guide" Ed. G. A. Grant; 1992). The resulting nucleoside linker conjugate is converted to the corresponding triphosphate by using the conditions described for the preparation of compound (6). Labelling of the triphosphate so produced is achieved by following the procedure described below for the preparation of compound (18).

Figure 6:
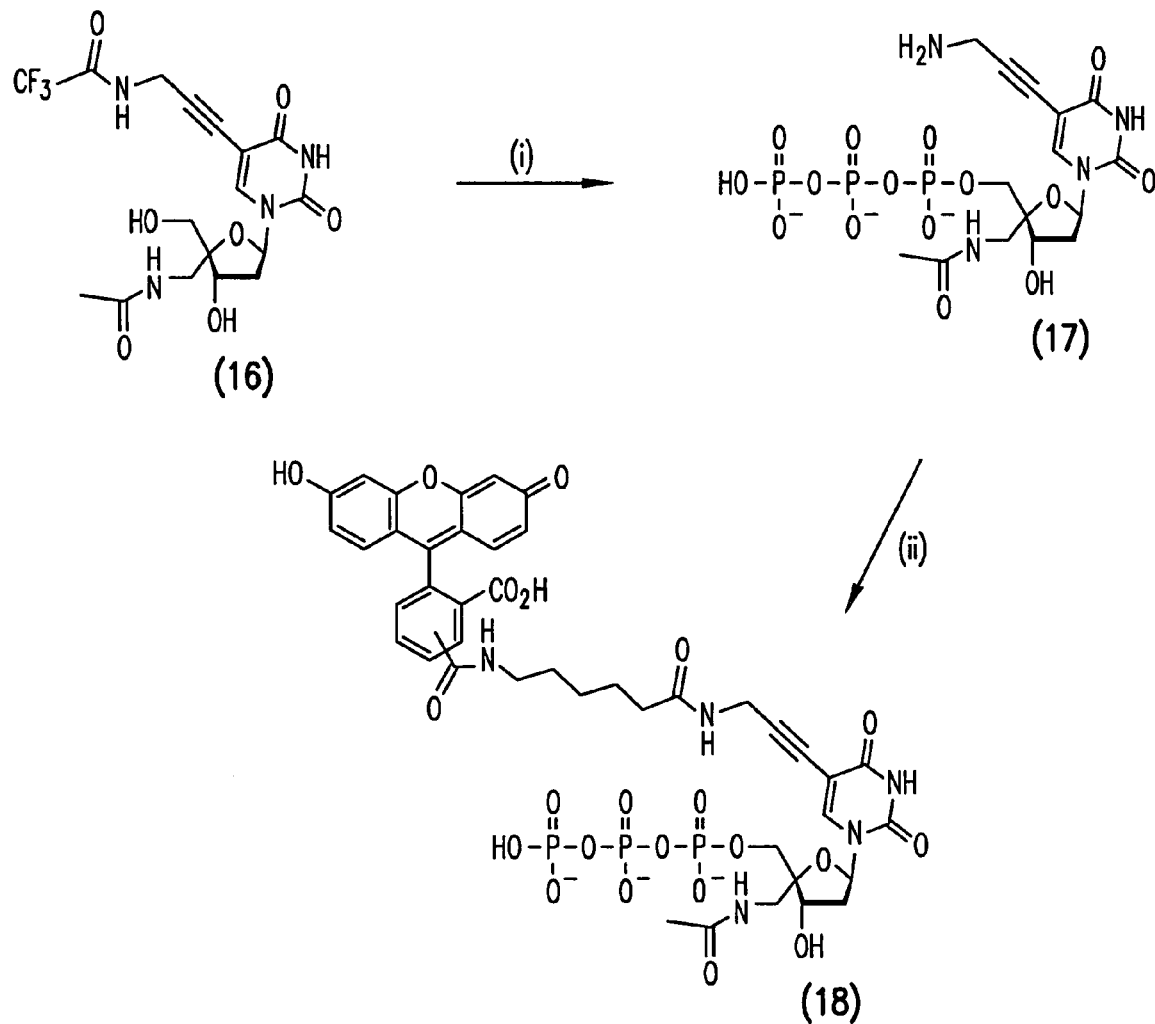
FIG. 6 shows a reaction scheme for synthesising a fluorescein-labelled nucleotide.

Nucleoside analogue (16) was converted to a nucleotide and a fluorescent label incorporated according to the reaction scheme of FIG. 6.

i) 5-(N-Trifluoroacetyl)propargylamino-4'-C-(acetylaminomethyl)-2'-deoxyuridine triphosphate (17)

5-(N-Trifluoroacetyl)propargylamino-4'-C-(acetylaminomethyl)-2'-deoxyuridine (16) (5.3 mg, 0.012 mmol) was treated with phosphorous oxychloride (0.04 g, 0.0244 mmol, 2.2 uL), tributylammonium pyrophosphate (0.25 mL of 0.5M solution) and tributylamine (0.019 mL) in trimethylphosphate (0.25 mL) and N,N-dimethylformamide (0.25 mL) according to the procedure used to prepare compound (6).

ii) 5-[N-Fluorescein-5(and-6-)carboxamidohexanoyl]propargylamino-4'-C-(acetylaminomethyl)-2'-deoxyuridine triphosphate (18)

5-(N-Trifluoroacetyl)propargylamino-4'-C-(acetylaminomethyl)-2'-deoxyuridine triphosphate (17) was dissolved in anhydrous DMSO at ambient temperature. 6-[Fluorescein-5(and-6)-carboxamidohexanoic acid N-hydroxysuccinamidyl ester and triethylamine were then added and the reaction mixture stirred at ambient temperature for 18 hours. Reaction mixture was then diluted with water and lyophilised for 48 hours. The crude material was then re-dissolved in 0.1M triethylammonium bicarbonate (1 mL) and subjected to preparative reverse phase HPLC purification using 0.1 triethylammonium bicarbonate/water as mobile phase.

EXAMPLE 4

Synthesis of Nucleoside Analogues 4'-C-(N-Acetylglycylaminomethyl)thymidine (19); 4'-C-(N-Leucylaminomethyl)thymidine (21) and 4'-C-(N-Glycylaminomethyl)thymidine (22) which Have a Blocking Group Attached Through an Amidase Cleavable Linker at the 4' Position.

Figure 7:
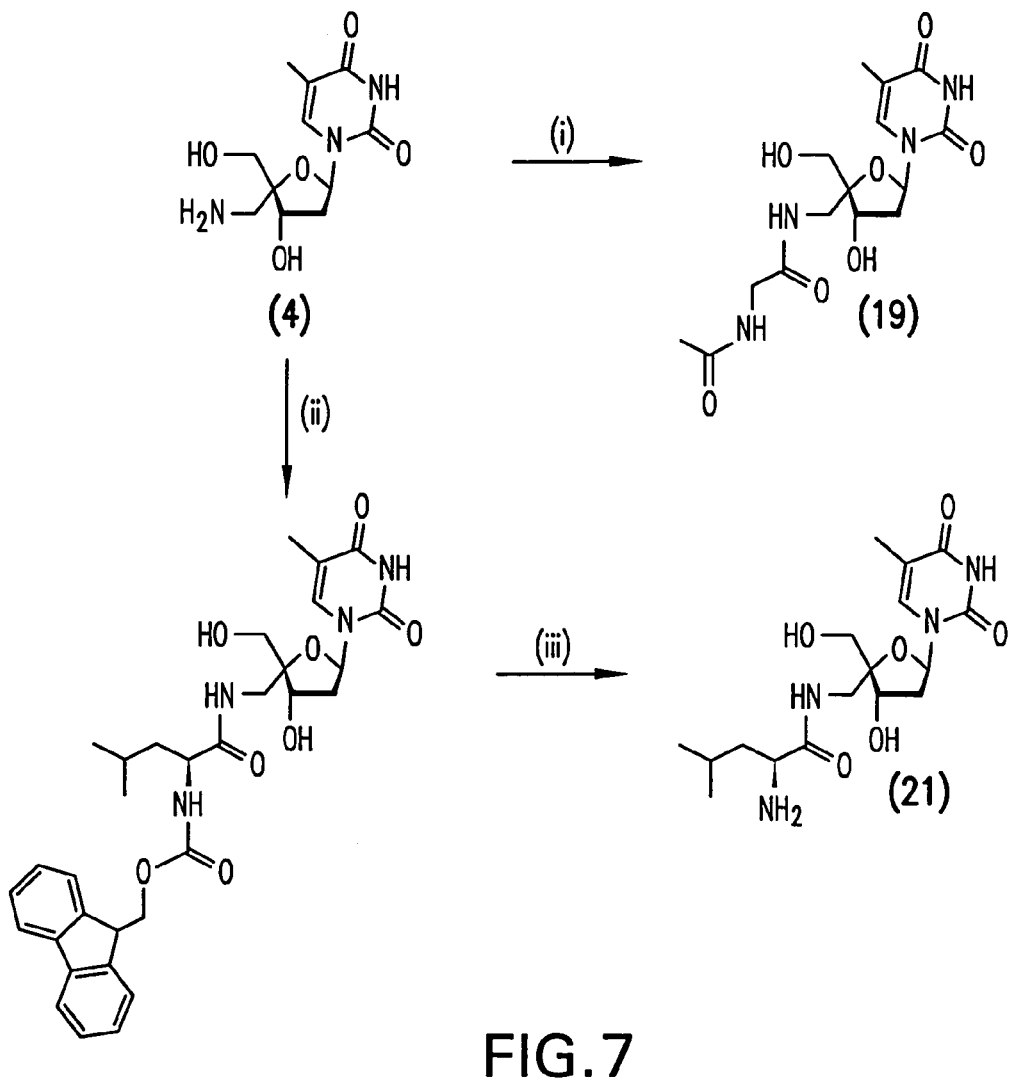
FIGS. 7 and 8 show reaction schemes for synthesising nucleoside analogues.

FIG. 7 shows a reaction scheme for synthesis of nucleoside analogues (compounds (19) and (21)) which have a blocking group attached through an amidase cleavable linker at the 4' position i) 4'-C-(N-Acetylglycylaminomethyl)thymidine (19)

4'-C-(Aminomethyl)thymidine (4) (0.025 g, 0.1 mmol), N-acetylglycine (0.023 g, 0.2 mmol) and TSTU (0.09 g, 0.3 mmol) were dissolved in anhydrous N,N-dimethylformamide (1 mL) at ambient temperature. Diisopropylethylamine (0.065 g, 0.5 mmol, 0.087 mL) was then added and the reaction mixture stirred for 18 hours at ambient temperature. The solvent was then removed under vacuum and the residue re-dissolved in 9:1 dichloromethane:methanol and eluted through a flash silica gel column with 9:1 dichloromethane:methanol. The title compound (19) was obtained as an amorphous solid on removal of solvent from the appropriate fractions (0.023 g). $\delta_H$(300 MHz, $CD_3OD$) 7.78(1H, s, H-6), 6.26(1H, dd, H-1'), 4.48(1H, dd, H-3'), 3.83(2H, s, glycyl $CH_2$), 3.60(2H, 2d, H-5'), 3.58(1H, d, 4'-C—$CH_2$), 3.42(1H, d, 4'-C—$CH_2$), 2.33(2H, m, H-2'), 2.00(3H, s, $CH_3CO$), 1.86(3H, s, 5-$CH_3$); ES +ve m/z 393$(M+Na)^+$.

ii) 4'-C-[N-(9-Fluorenylmethyloxycarbonyl)leucylaminomethyl]thymidine (20)

4'-C-(Aminomethyl)thymidine (4) (0.025 g, 0.1 mmol), N-(9-fluorenylmethyloxycarbonyl)leucine (0.071 g, 0.2 mmol), TSTU (0.09 g, 0.3 mmol) and diisopropylethylamine (0.065 g, 0.5 mmol, 0.087 mL) were combined in DMF (1 mL) according to the procedure used to prepare compound (19). The title compound (20) was obtained as an amorphous solid (0.056 g). $\delta_H$(300 MHz, CD3OD) 7.86–7.37(8H, m, Fmoc), 7.74(1H, s, H-6), 6.24(1H, dd, H-1'), 4.56(1H, dd, H-3'), 3.68(2H, 2d, H-5'), 3.40(2H, 2d, 4'-C—$CH_2$), 2.37 (2H, m, H-2'), 1.70(3H, m, leucyl CH, $CH_2$), 1.66(3H, s, 5-$CH_3$), 1.05(3H, d, leucyl $CH_3$), 1.02(3H, d, leucyl $CH_3$); ES +ve m/z 607$(M+H)^+$, 629$(M+Na)^+$.

iii) 4'-C-(N-Letcylaminomethyl)thymidine (21)

4'-C-[N-(9-Fluorenylmethyloxycarbonyl)leucylaminomethyl]thymidine (20) was dissolved in N,N-dimethylformamide. Piperidine was then added and the solution stirred at ambient temperature for 6 hours. The solvent was then removed under vacuum and the residue re-dissolved in water. The aqueous solution was then washed with toluene and 40–60 petroleum ether, and then separated and lyophilised. The lyophilised product was further purified by flash column chromatography (85:15 dcihloromethane:methanol) to give the title compound (21) as a resin. $\delta_C$(300 MHz, $D_2O$) 7.47(1H, s, H-6), 6.13(1H, dd, H-1'), 4.65(1H, dd, H-3'), 3.34(2H, 2d, H-5'), 3.28(1H, d, 4'-C—$CH_2$), 3.00(1H, d, 4'-C—$CH_2$), 2.50(1H, dd, leucyl CH), 2.33(2H, m, H-2'), 1.73(3H, s, 5-$CH_3$), 1.11(2H, m, leucyl $CH_2$), 0.76(3H, d, leucyl $CH_3$), 0.71(3H, d, leucyl $CH_3$); ES +ve m/z 385$(M+H)^+$.

The nucleotide equivalent of compound (19) is prepared according to the methods for phosphorylating compounds (5) or (7) (see above).

The nucleoside equivalent of compound (21) is prepared by phosphorylation of compound (20) according to the methods for phosphorylating compound (7) (see above) prior to the deprotection reaction of compound (20) to form compound (21) as described above.

Figure 8:
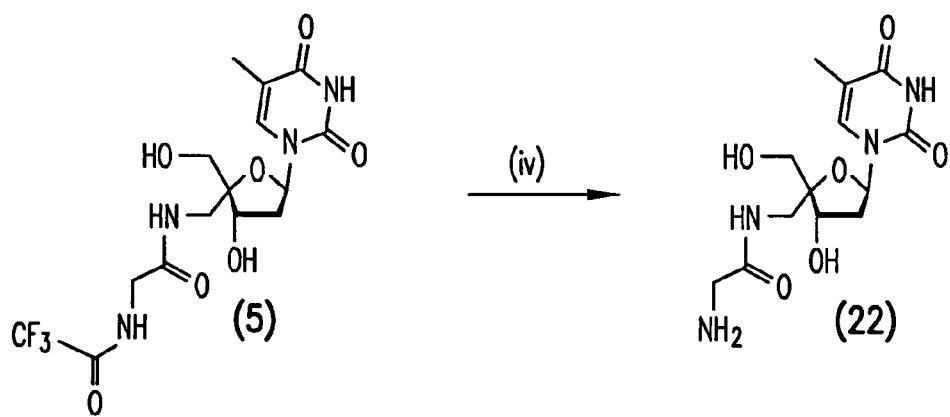

FIG. 8 shows a reaction scheme for synthesising a further nucleoside having an amidase cleavage site at the 4' position (compound (22)).

i) 4'-C-(N-Glycylaminomethyl)thymidine (22)

4'-C-(N-trifluoroacetylglycylaminomethyl)thymidine (5) (17 mg, 0.4 mmol) was dissolved in concentrated aqueous ammonia solution (1 mL) and allowed to stand overnight at ambient temperature. The reaction mixture was then lyophilised to give the title compound (22) as a colourless resin (0.0088 g, 67%). $\delta_H$(300 MHz, $D_2O$) 7.46(1H, s, H-6), 6.14(1H, dd, H-1'), 4.48(1H, dd, H-3'), 3.70(2H, s, glycyl $CH_2$), 3.47(2H, 2d, H-5'), 3.40(2H, 2d, 4'-C—$CH_2$), 2.35 (2H, m, H-2'), 1.73(3H, s, 5-$CH_3$); ES +ve m/z 329$(M+H)^+$.

A nucleosides having formula (22) is converted to the corresponding triphosphate by using the conditions described for the preparation of compound (8).

Figure 9:
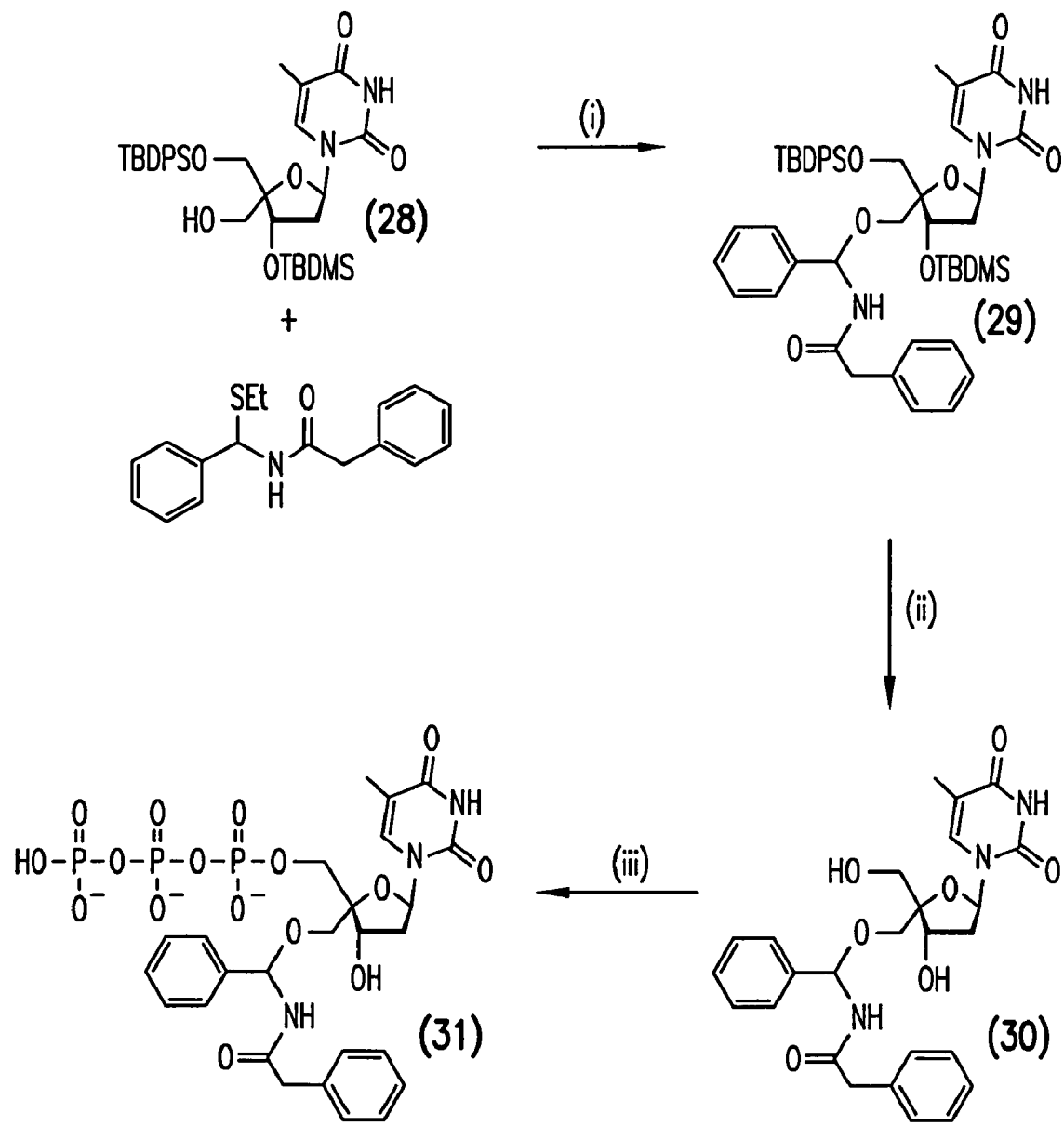
FIGS. 9 and 10 show reaction schemes for synthesising nucleotide analogues.

FIG. 9 shows a reaction scheme for synthesising a nucleotide having a penicillin amidase cleavage site at the 4' position (compound (31)).

i) N-{α-[3'-O-((teributyl)dimethylsilyl)-5'-O-((tertbutyl) diphenysilyl)-4'-methyloxythymidyl] phenyl}phenylacetamide (29).

3'-O-[(tertbutyl)dimethylsilyl]-5'-O-[(tertbutyl)diphenylsilyl]-4'-hydroxymethyl thymidine (Marx et. al. *Helv. Chim. Acta.* 1996, 79, 1980–1994 and references cited therein) (28) is treated with N-[α-thioethylphenyl]phenyl acetamide (24) and N-iodosuccinimide in accordance with the procedure described for the preparation of compound (25) to obtain the title compound (29).

ii) N-{α-[4'-methyloxythymidyl]phenyl}phenylacetamide (30).

N-{α-[3'-O-((tertbutyl)dimethylsilyl)-5'-O-((tertbutyl) diphenylsilyl)-4'-methyloxythymidyl] phenyl}phenylacetamide (29) is treated with tetrabutylammonium fluoride in tetrahydrofuran in accordance with the procedure used to prepare compound (26) to obtain the title compound (30).

iii) N-{α-[4'-methyloxythymidyl]phenyl}phenylacetamide triphosphate (31).

N-{α-[4'-methyloxythymidyl]phenyl}phenylacetamide (30) is treated with 2-chloro-4H-1,3,2-dioxaphosphorin-4-one, pyridine, tributylammonium pyrophosphate, iodine solution and tributylamine in accordance with the procedure used to prepare compound (27) to obtain the title compound (31).

Labelling of the triphosphates so produced is achieved by following the procedure described for the preparation of compound (18).

EXAMPLE 5

Synthesis of a Nucleotide with an Enzyme (Penicillin Amidase) Cleavable Blocking Group at the 3'-Position.

Figure 10:
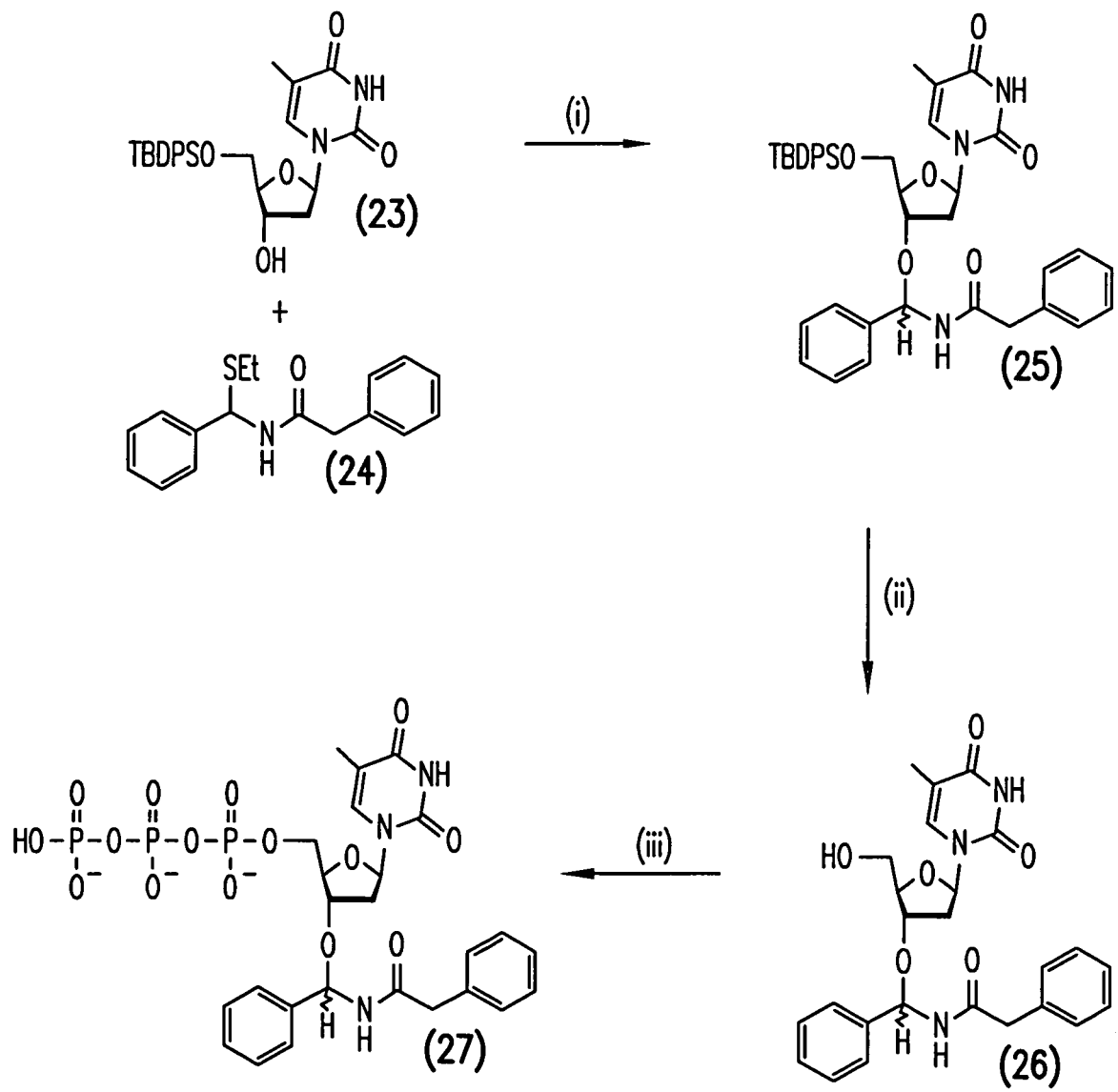

FIG. 10 shows a reaction scheme for the synthesis of a nucleotide of formula (27).

i) N-[α-(5'-O-terbutyldiphenylsily N-3'-O-thymidyl)-phenyl)]-phenylacetamide (25)

5'-O-tertbutyldimethylsilyl thymidine (0.5 g, 1 mmol) (23) and N-[α-thioethylphenyl]phenyl acetamide (Flitsch et. al. *Tetrahedron Letters* 1998, 39, 3819–3822 and references cited therein; Flitsch et. al. PCT WO 97/20855) (24) (0.28 g, 1 mmol) were dissolved in anhydrous dichloromethane (5 mL) at ambient temperature. Crushed, activated 4A molecular sieves (1 g) were then added and the mixture stirred for 15 minutes at ambient temperature before cooling to 0 C. on an ice bath N-Iodosuccinimide (0.33 g, 1.5 mmol) was then added as a solid to the cooled solution. The resulting solution was then stirred for 3 hours at 0 C. Saturated sodium thiosulfate solution (10 mL) was then added and the organic layer separated. The aqueous layer was back extracted with a portion of dichloromethane (10 mL). The combined organic extracts were then dried over magnesium sulfate, filtered and then concentrated under vacuum. Purification by flash column chromatography (1:1 40–60 petrol ether:ethyl acetate) gave the title compound (1:1 mixture of diastereoisomers) as a white foam on removal of solvent from the appropriate fractions. Yield=0.4 g (55%). δ(300 MHz, d$_6$-DMSO) 11.35(1H, s, N$^3$—H), 9.05(1H, 2d, amide N—H), 7.59–7.15(22H, m, Ph$_2$Si, Ph, PhCH$_2$CO, α-H, H-6), 6.23–6.14(1H, m, H-1'), 4.46–3.29(4H, m, H-5', H-4', H-3'), 2.48–2.17(2H, m, H-2'), 1.44, 1.41(3H, 2s, 5-CH$_3$), 0.98, 0.95(9H, 2s, tBuSi); δ(75.45 MHz, d$_6$-DMSO) 170.87, 163.54, 150.38, 139.21, 135.85, 135.23, 134.88, 132.85, 132.26, 130.02, 129.04, 128.28, 128.24, 127.97, 126.30, 109.74, 84.40, 83.91, 83.67, 83.47, 79.03, 78.60, 76.54, 76.40, 63.97, 59.72, 55.33, 48.57, 42.23, 37.45, 26.60, 20.74, 18.83, 14.06, 11.72.

ii) N-[α-(3'-O-thymidyl)-phenyl)]-phenylacetamide (26)

N-[α-(5'-O-tertbutyldiphenylsilyl-3'-O-thymidyl)-phenyl)]-phenylacetamide (25) (0.4 g, 0.56 mmol) was dissolved in tetrahydrofuran (10 mL) at ambient temperature. A 1M solution of tetrabutylammonium fluoride in tetrahydrofuran (0.56 mL) was then added to the solution of the nucleoside. After stirring for 4 hours methanol (2 mL) was added and the solvent removed under vacuum to give a white foam. Flash column chromatography (95:5 dichloromethane:methanol) gave the title compound as a white foam (mixture of diastereoisomers). Yield=0.22 g (85%). δ(300 MHz, d$_6$-DMSO) 11.30(1H, s, N$^3$—H), 9.03(1H, 2d, amide N—H), 7.67, 7.63(1H, 2s, H-6), 7.43–7.18(11H, m, Ph, PhCH$_2$CO, α-H), 6.19–6.11(1H, m, H-1'), 5.07(1H, t, br, 5'-OH), 4.28–3.98(3H, m, H-4', H-3'), 3.56(2H, m, H-5'), 2.40–2.20(2H, m, H-2'), 1.75, 1.74(3H, 2s, 5CH$_3$); δ(75.45 MHz, d$_6$-DMSO) 170.84, 170.78, 139.44, 135.94, 135.88, 129.02, 128.28, 128.26, 128.23, 128.15, 126.43, 126.35, 109.49, 84.65, 83.75, 78.85, 77.20, 76.95, 59.72, 42.20, 20.74, 14.06, 12.24.

iii) N-[α-(3'-O-thymidyl)-phenyl)]-phenylacetamide triphosphate (27)

N-[α-(3'-O-thymidyl)-phenyl)]-phenylacetamide (26) (0.11 g, 0.24 mmol), 2-chloro-4H-1,3,2-dioxaphosphorin-4-one (0.24 mL of 1M solution in 1,4-dioxane), pyridine (0.24 mL), tributylammonium pyrophosphate (0.72 mL of 1M solution in DMF), iodine (0.16 g dissolved in 7.2 mL pyridine/0.14 mL water) and tributylamine were combined according to the procedure used to prepare compound (8).

EXAMPLE 6

Preparation of a Nucleotide with a Penicillin Amidase Cleavable Linker and Penicillin Amidase Cleavable 3'-Blocking Group.

Figure 11:
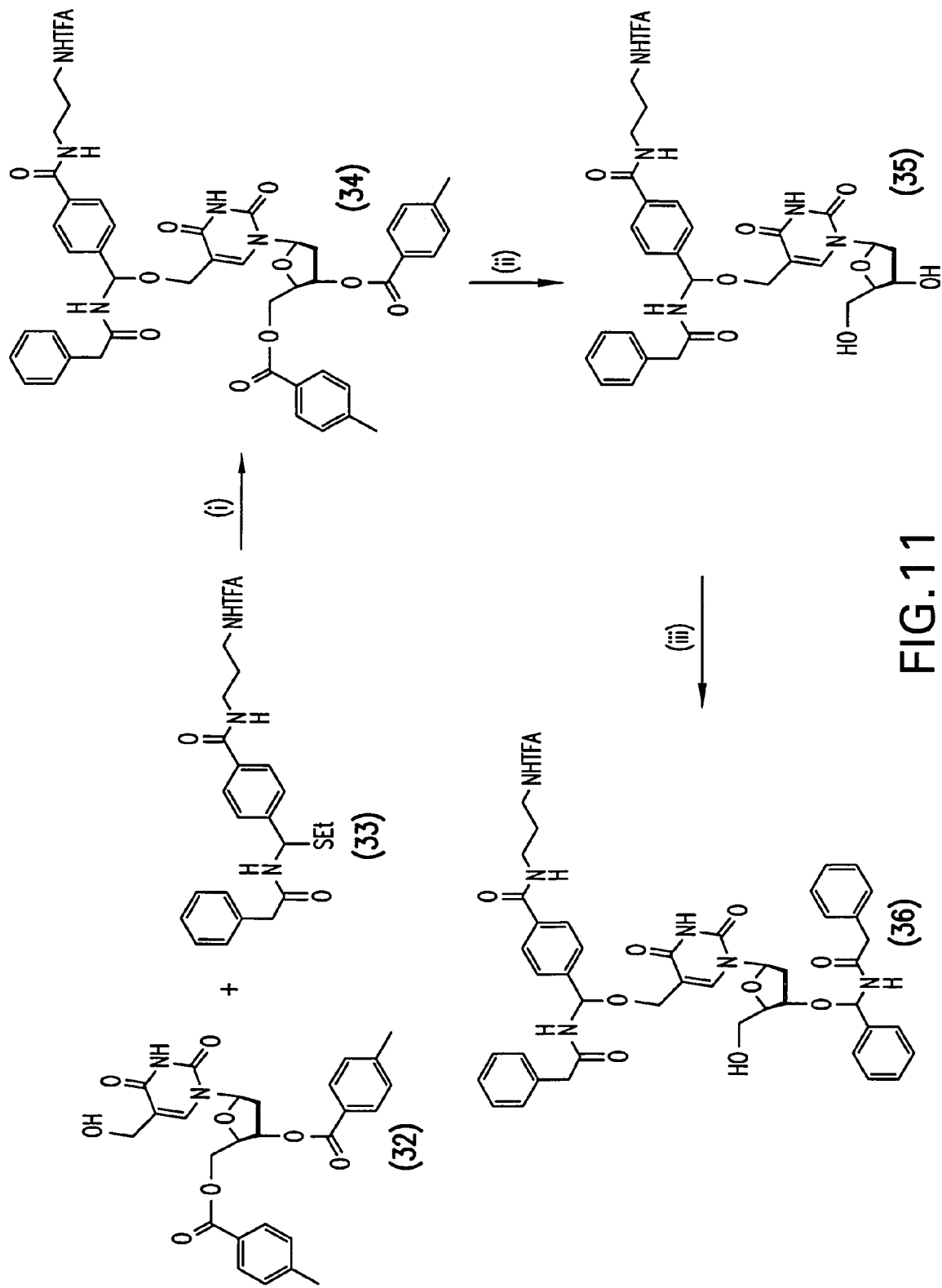
FIG. 11 shows a reaction scheme for synthesising a nucleoside analogue.

FIG. 11 shows a reaction scheme for the synthesis of a compound of formula (36).

i) 5-Hydroxymethyl-5',3'-di-O-p-toluyl-2'-deoxyuridine (32) (prepared using well established procedures described, for example, in Chemistry of Nucleosides and Nucleotides; Volume 1. Ed. L. B. Townsend, 1988) and N-[α-thioethyl-N'-trifluoroacetylaminopropyl benzamide] phenylacetamide (33) (prepared from procedures in Katritzky et al.; Synthesis, 1993, 445–456) is combined in the presence of N-iodosuccinimide according to the procedure used to obtain compound (25) to afford the intermediate (34).

ii) Compound (34) is converted to the intermediate (35) by treatment with sodium methoxide in methanol, followed by ethyl trifluoroacetate in methanol.

iii) Compound (35) may then be converted to nucleoside (36) using the procedure outlined for the preparation of compound (26). Conversion to a triphosphate is achieved by using the procedure described for the preparation of compound (27). Labelling of the triphosphate so produced is achieved by following the procedure described for the preparation of compound (18).

EXAMPLE 7

Preparation of a Nucleoside Analogue Containing a Fluorescent Group Attached via an Enzyme Cleavable Linker.

Figure 12:
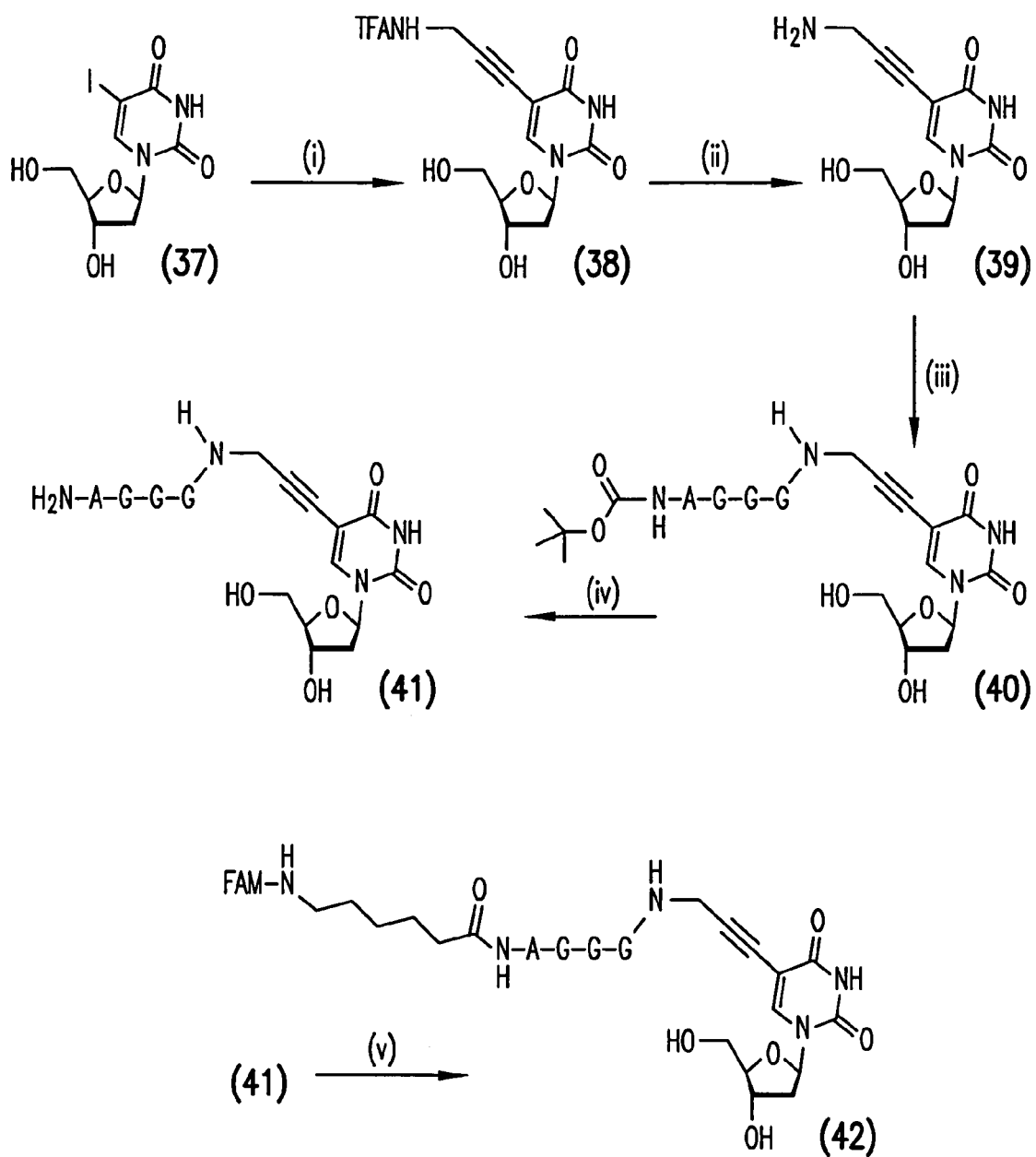
FIG. 12 shows a reaction scheme for synthesising a fluorescein-labelled nucleoside.

FIG. 12 shows a reaction scheme for the synthesis of a compound of formula (42).

i) 5-iodo-2'-deoxyuridine (37) was reacted with TFAproparglyamine in a palladium (Pd(PPh$_3$)$_4$) catalysed coupling reaction in the presence of CuI and DMF to introduce the trifluoroacetylproparglyamino arm.

ii) 5-propargylamino-2'-deoxyurdine (39) was then obtained by stirring with concentrated aqueous ammonia iii) Coupling the tetrapeptide N-Boc-Ala-Gly-Gly-Gly-OH (Bachem Ltd, UK) (tBOC-NH-AGGG-OH) to (39) was achieved by treatment with EDCI.HCl and N-hydroxysuccinimide in dimethylformamide.

iv) The N-terminal Boc group was then removed by treatment with 50% trifluoroacetic acid in dichloromethane to give the peptide-nucleoside conjugate (41).

v) Labelling of the tetrapeptide N-terminus was achieved by treating (41) with a molar excess of fluorescein hexanoic acid NHS ester (6-(Fluorescein-5(and-6) carboxamidohexanoic acid NHS ester) in triethylamine/dimethylformamide. The product (42) was purified by thin layer chromatography.

EXAMPLE 8

Enzyme Cleavage Reactions a) Cleavage of the 4' Blocking Group from Compound (22)

1 mg of 4'-C-(N-Glycylaminomethyl)thymidine (22) or 4'-C-(N-Acetylglycylaminomethyl)thymidine (19) is incubated at 37° C. in 60 mM sodium phosphate buffer pH 7.0 with 0.5 units aminopeptidase M (Calbiochem 164598), to a final volume of 200 ul.

b) Cleavage of 4' Blocking Group from Compound (21)

1 mg of 4'-C-(N-Leucylaminomethyl)thymidine (21) is incubated at 37° C. in 47 mM sodium phosphate pH 7.2 with 3.3% methanol and 0.25 units leucine aminopeptidase (Sigma L0632), to a final volume of 200 ul.

c) Cleavage of 3' Blocking Group from Compound (26)

1 mg of N-[α-(3'-O-thymidyl)-phenyl)]-phenylacetamide (26) is incubated at 37° C. in 50 mM potassium phosphate pH 7.5 with 2 units of penicillin amidase (Fluka P3319), to a final volume of 200 ul.

The products resulting from a), b) or c) above are analysed by thin layer chromatography using reverse phase plates with 10% acetonitrile in water or by electrospray mass spectrometry. Successful cleavage reactions yield nucleosides running concurrently with 4'-aminomethylthymidine which is used as a standard.

Mass spectrometric detection of the thymidine daughter ion (mass 242) arising from fragmentation of 4'-C-(N-aminomethyl)thymidine suggested that enzyme induced cleavage of the amino acid from the leucyl-containing compound (4'-C-(N-Leucylaminomethyl)thymidine (21)) had occurred.

d) Cleavage of the Fluorophore from the Nucleoside of Compound (42)

1 mg of the substrate (42) was dissolved in a buffer containing 0.1M sodium phosphate, pH 6.3, 5 mM EDTA, 60 μM β-Mercaptomethanol. Enzyme digestion was started by adding 1 unit of papain (150 units/mg, Europa Ltd) in a final reaction volume of 200 μl followed by incubation at 50° C. for 2 h. The reactions were spotted on a thin layer chromatography plate and air dried before chromatography for 20 min. in a 4:1 mixture of dichloromethane/methanol.

Following thin layer chromatography, the undigested substrate control migrated from the origin with no ultraviolet light absorbing material present at the origin and a clear fluorescence observable proximal to the solvent front. In contrast the non-fluoresceinated nucleoside control appeared as a strongly ultraviolet light absorbing material that showed little or no migration from the origin. As evidenced by thin layer chromatography, the papain digested material resulted in the production of a non-fluorescent, strongly ultraviolet light absorbing material at the origin that was consistent with the cleavage of the linker and separation of the nucleoside from the fluor.

EXAMPLE 9

DNA Polymerase Assays

DNA polymerase assays were performed using Sequence 1 as primer and Sequence 2 as template.

Sequence 1 5'[Cy3]TAACTCATTAACAGGATC 3'

Sequence 2 5'AT TCG CGG TAT TCT GGT ATG AAG CTT TTA GAT CCT GTT AAT GAG TTA GTA3'

The template (Sequence 2) was designed such that the base (underlined) immediately adjacent to the 3' end of the hybridised primer is complementary to the nucleotide test compound. Nucleotide test compounds were compounds (6) (4'-C-(glycylaminomethyl)thymidine triphosphate), (8) (4'-C-(N-trifluoroacetyaminomethyl)thymidine triphosphate) and (9) (4'-C-(aminomethyl)thymidine triphosphate) as described above.

Primer extension reactions were performed using the above primers in the presence of 40 to 80 μM of nucleotide triphosphates. Positive control reactions contained all four native nucleotide triphosphates. For the other reactions the TTP was replaced with either a 2:1 ratio of TTP/dTTP for the terminator control, or entirely by the test compound The enzymes were used at a final concentration of 0.175 units/μl and a magnesium ion concentration of 2.5 mM in buffers supplied by the manufacturer. The primer and template concentrations were 0.5 pmol/μl and 2 pmol/μl respectively.

Extension reactions with thermophilic enzymes were performed by initially denaturing the fully assembled reactions at 70° C. for 5 min. followed by 45° C. for 20–40 minutes. The following enzymes were used: Taq DNA polymerase (Taq); Thermosequenase (TS); Thermosequenase II (TSII); Thermosequenase E (TSE), Tfl DNA polymerase (Tfl); Tth DNA polymerase (Tth), deltaTts DNA polymerase (deltaTts), deltaTts D DNA polymerase (dettaTTSD) (all from APBiotech); Pfu DNA polymerase (Pfu) (Stratagene Ltd); Vent™ DNA polymerase (Vent) (New England Biolabs).

Extension reactions preformed with mesophilic polymerases were carried out by mixing all the components of the reaction except the enzyme and heating to 70° C. for 5 min. After the reactions had cooled to room temperature 0.175 units of the enzyme were added and the reactions heated to 37° C. for 20–40 minutes. The following enzymes were used: T7 DNA polymerase (T7); Sequenase 2™ (Seq); Klenow fragment of DNA polymerase 1 (Klen); phi-29 DNA polymerase (Phi-29); T4 DNA polymerase (T4) (all from AP Biotech) and Bst DNA polymerase (Bst) (Cambio Ltd).

Reverse transcriptase reactions were performed essentially as described above for thermophilic and mesophilic enzymes. The template for these reactions was the RNA equivalent of sequence 2. All the thermophilic enzymes were assayed in Tth reaction buffer (Cambio Ltd, Cambridge UK) containing 2.5 mM Manganese ions. The following enzymes were used: Thermosequenase (TS1); Thermosequenase II (TSII); delta Tts DNA polymerase (deltaTts); delta Tts D DNA polymerase (deltaTtsD) (all from APBiotech); Retrotherm reverse transcriptase (Retroth) (Cambio Ltd); Tth DNA polymerase (Tth) (Cambio Ltd.).

Mesophilic reverse transcriptases (AMV RT; MuLV RT; SAV RT and HIV RT all from APBiotech) were assayed in their respective buffers with a final enzyme concentration of 4 units/µl.

The reactions were stopped by adding a 0.5 volume aliquot of 80% formamide containing 0.1% (w/v) bromophenol blue and 0.1% (w/v) cresol blue. The reaction products were separated by denaturing gel electrophoresis at a constant power of 45 W on 16% polyacrylamide gels containing 50% urea.

Gels were scanned for Cy3 fluorescence on a Molecular Dynamics Fluorimager and the data analysed using Molecular Dynamics ImageQuant 5 software.

The incorporation of a test nucleotide triphosphate results in the appearance on a polyacrylamide gel of a single band corresponding to a single base extension product. If, however, the enzyme adds additional bases then further bands would be observed that corresponded to either the full-length product or positions of other complementary bases in the template.

The results were graded as follows:
- No extension within assay time
+/- up to 25% of primer extended by at least one base within assay time
+ up to 50% of primer extended by at least one base within assay time
++ up to 75% of primer extended by at least one base within assay time
+++ essentially all primer extended by at least one base within assay time
T Incorporation results in termination
E Incorporation permits further chain extension
T/E Predominant product is primer extended by one base, but evidence of some further extension also observed.

TABLE 1 shows the results of Thermostable DNA polymerase reactions

|  | compound (6) |  | compound (8) |  | compound (9) |  |
|---|---|---|---|---|---|---|
| Taq | +/- | T | +/- | T | +/- | T |
| TS | + | T | + | T | + | T |
| TSII | + | T | + | T | + | T |
| Pfu | - |  | - |  | - |  |
| Vent | +/- | T | +/- | T | +/- | T |
| TSE | ++ | T | ++ | T | ++ | T |
| Tfl | +/- | T | +/- | T | +/- | T |
| Tth | + | T | ++ | T | ++ | T |
| delta Tts | + | T | + | T | +T | T |
| delta TTSD | ++ | T | ++ | T/E | ++ | T/E |

TABLE 2 shows the results of Mesophilic DNA polymerase reactions

|  | compound (6) |  | compound (8) |  | compound (9) |  |
|---|---|---|---|---|---|---|
| T7 | +/- | T/E | +/- | T/E | +/- | T/E |
| Bst | + | T | + | T | + | T |

TABLE 2-continued shows the results of Mesophilic DNA polymerase reactions

|  | compound (6) |  | compound (8) |  | compound (9) |  |
|---|---|---|---|---|---|---|
| Seq | + | T | + | T | + | T |
| Klen | - |  | - |  | - |  |
| phi-29 | +/- | T | +/- | T | +/- | T |
| T4 | + | T | + | T | + | T |

TABLE 3 shows the results of reactions with Thermostable polymerases under reverse transcription conditions

|  | compound (6) |  | compound (8) |  | compound (9) |  |
|---|---|---|---|---|---|---|
| TS I | + | T/E | + | T/E | + | T/E |
| TS II | + | E | + | E | ++ | E |
| Retroth. | ++ | E | ++ | E | +++ | E |
| Tth | +++ | T | +++ | T | +++ | T |
| delta Tts | +++ | T | +++ | T | +++ | T |
| delta TtsD | +++ | E | +++ | E | +++ | E |

TABLE 4 shows the results of reactions with Mesophilic reverse transcriptase.

|  | compound (6) |  | compound (8) |  | compound (9) |  |
|---|---|---|---|---|---|---|
| AMV RT | - |  | - |  | - |  |
| MuLV RT | ++ | E | ++ | E | ++ | E |
| SAV RT | + | E? | ++ | E | ++ | E |
| HIV RT | +++ | E | +++ | E | +++ | E |

SUMMARY

Compounds (6) (4'-C-(glycylaminomethyl)thymidine triphosphate), (8) (4'-C-(trifluoroacetylaminomethyl)-thymidine triphosphate) and (9) (4'-C-(aminomethyl)thymidine triphosphate) were effective substrates for a range of polymerases and that their incorporation resulted in termination. When reverse transcriptase conditions were used, some extension was observed suggesting that a larger blocking group may be required for those nucleotides when used with certain enzymes under certain specific conditions.

The invention claimed is:

1. A compound of Formula I

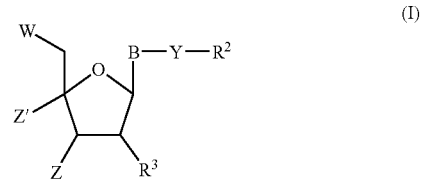

wherein
  W is a phosphate group
  B is a base
  Y is a linker comprising an enzyme-cleavable group
  $R^2$ is a reporter moiety
  $R^3$ is selected from H or OH
  Z and Z' are selected from H, OH, or a group X—$R^1$, wherein X is a linker comprising an enzyme-cleavable group and R¹ is a polymerase enzyme blocking group, provided that at least one of Z and Z' is X—R¹.

2. The compound of claim 1 wherein W is a triphosphate.

3. The compound of claim 1 wherein B is selected from the bases A, C, G and T or their analogues.

4. The compound of claim 1 wherein the enzyme-cleavable groups, X and Y, are the same.

5. The compound of claim 1 wherein X and Y are groups cleavable by enzymes selected from esterases, phosphatases, peptidases, amidases, glycosidases or phosphorylases.

6. The compound of claim 1 wherein X and/or Y is a group cleavable by an amidase.

7. The compound of claim 1 wherein R² is a fluorophore selected from the group consisting of fluoresceins, rhodamines, coumarins, BODIPY™ dyes, cyanine dyes and squarate dyes.

8. The compound of claim 1 wherein R¹ is selected from the group consisting of CH₃, glycyl and leucyl groups.

9. The compound of claim 1 wherein Z' is X—R¹ and Z is OH.

10. The compound of claim 1 wherein R¹ is not a reporter moiety.

11. A chemical intermediate selected from the group consisting of: 4'-C-(Glycylaminomethyl)thymidine triphosphate; 4'-C-(N-trifluoroacetylaminomethyl)thymidine triphosphate; 4'-C-(Aminomethyl)thymidine triphosphate; 5-(N-Trifluoroacetyl)propargylamino-4'-C-(acetylaminomethyl)-2'-deoxyuridine; 4'-C-(N-Acetylglycylaminomethyl)thymidine; 4'-C-(N-Leucylaminomethyl)thymidine; 4'-C-(N-Glycylaminomethyl)thymidine (shown in FIG. 8); N- {α-[4'-methyloxythymidyl]phenyl}phenylacetamide triphosphate; N- [α-(3'-O-thymidyl)-phenyl)]-phenylacetamide triphosphate, N- {α-[3'-O-(5-N-(α-methyloxy-N'-trifluoroacetylaminopropyl benzamide) phenylacetamide-2'-deoxyuridyl]-phenyl }-phenylacetamide and a compound of formula:

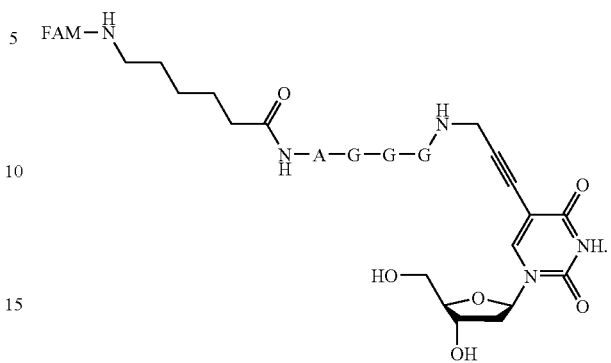

(42)

12. A set of nucleotides containing at least one compound of Formula I.

13. The set of nucleotides of claim 12 comprising each of the four natural bases A, G, C and T (or their analogue).

14. The set of nucleotides of claim 12 containing at least two compounds of Formula I having different bases, B, and wherein each compound of Formula I has a different reporter moiety, R².

15. The set of nucleotides of claim 12 containing four compounds of Formula I wherein each compound has a different base, B, such that each of the bases A, G, C and T, or analogues thereof, are present and each of the four compounds of Formula I has a reporter moiety which is distinguishable from the reporter moieties of each of the other three compounds of Formula I.

* * * * *